United States Patent [19]

Boyer et al.

[11] Patent Number: 5,674,998
[45] Date of Patent: Oct. 7, 1997

[54] C-4' MODIFIED ADENOSINE KINASE INHIBITORS

[75] Inventors: Serge H. Boyer, San Diego; Mark D. Erion, Del Mar; Bheemarao G. Ugarkar, Escondido, all of Calif.

[73] Assignee: Gensia Inc., San Diego, Calif.

[21] Appl. No.: 486,161

[22] Filed: Jun. 7, 1995

Related U.S. Application Data

[63] Continuation-in-part of Ser. No. 812,916, Dec. 23, 1991, abandoned, and Ser. No. 191,282, Feb. 3, 1994, Pat. No. 5,506,347, said Ser. No. 812,916, is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 18, 1989, abandoned.

[51] Int. Cl.⁶ .................. C07H 19/044; C07H 19/14
[52] U.S. Cl. .............. 536/27.13; 536/27.2; 536/27.21; 536/27.23; 536/27.62; 544/254; 544/262; 544/264; 544/265; 544/266; 544/267; 544/271; 544/272; 544/273; 544/277; 544/280
[58] Field of Search ...................... 536/4.1, 27.12, 536/27.4, 27.62, 27.13, 27.21, 27.23; 544/264, 254, 262, 280, 265, 266, 267, 271, 272, 273, 277

[56] References Cited

U.S. PATENT DOCUMENTS

| | | |
|---|---|---|
| 4,455,420 | 6/1984 | Kazlauskas . |
| 4,904,666 | 2/1990 | Friebe . |
| 5,506,347 | 4/1996 | Erion et al. .................. 536/4.1 |

FOREIGN PATENT DOCUMENTS

| | | |
|---|---|---|
| 0 496 617 | 7/1992 | European Pat. Off. . |
| WO 94/18215 | 8/1994 | WIPO . |
| WO 94/17803 | 8/1994 | WIPO . |

OTHER PUBLICATIONS

Achterberg et al., *Biochem. J.*, 235, 13–17 (1986).
Barker, R. et al., *J. Org. Chem.*, 26: 4605 (1961).
Barton, D. H. et al., *Pure Appl. Chem.* 53:15 (1981).
Bontemps et al., *Proc. Natl. Acad. Sci. USA*, 80, 2829–33 (1983).
Burke et al., *J. Neurochem*, 51: 1541 (1988).
Berkowitz, W. F. et al., *J. Org. Chem.* 52:1119 (1987).
Caldwell and Henderson, *Cancer Chemother. Rep.*, 2, 237–46 (1971).
Cheng, C.C. *J. Org. Chem.* 21:1240 (1956).
Cossy J. et al., *Tet Lett* 28: 4547 (1987).
Cottam, H.B., et al., *J. Med. Chem.*, 27, 119–27 (1984).
Davies et al., *Biochem. Pharmacol.*, 35, 3021–29 (1986).
Davies et al., *Biochem. Pharmacol.*, 33, 347–55 (1984).
Fetizon, M. et al., *Chem. Soc. Chem Comm.* 382 (1972).
Firestein et al., *J. Immunology* 154, 326–34 (1995).
Gewald, R., *Z. Chem.* 1, 349 (1961).
Green, J. *Supramol. Structure*, 13:175–182 (1980).
Henderson et al., *Cancer Chemotherapy Rep.* Part 2, 3, 71–85 (1972).
Inokawa, S. et al., *Carbohydrate Res.* 30: 127 (1973).
Jefford, C.W. et al., *JACS* 94: 8905 (1972).
Johnson, C.R. et al., *J. Org. Chem.* 59: 5854 (1994).
Juaristi, E. et al., *Tet Lett* 25:3521 (1984).
Keil et al., *Life Sciences* 5, 171–76 (1992).
Kobayashi, S., *Chem. Pharm. Bull.*, 21, 941–51 (1973).
Koll P. et al., *Ang. Chem. Int. Ed. Eng.*, 25: 368 (1986).
Leonard, N.J. et al., *J. Heterocyclic Chem.* 3: 485 (1966).
Newby et al., *Biochem. J.*, 214, 317–323 (1983).
Miller et al., *J. Biol. Chem.*, 254, 2346–52 (1979).
Molander, G.A. et al., *JACS* 109: 453 (1987).
Mori, K. et al., *Tetrahedron* 43: 2229 (1987).
Pak et al., *Soc. for Neuroscience Abs.*, 20, 149.2 (1994).
Paquette, L.A. et al., *JACS* 108: 3841 (1986).
Pecquet, P. et al., *Heterocycles* 34: 739 (1992).
Phillis et al., *Life Sciences*, 53, 497–502 (1993).
Prescott et al., *Nucleosides & Nucleotide*, 8, 297 (1989).
Redlich, H. *Angew. Chem.* 101: 764 (1989).
Romming, C. et al., *Act. Chem. Scan. B.* 40: 434 (1986).
Rosemeyer, H. and Seela, F., *Helv. Chim. Acta*, 71, 1573–85 (1988).
Samano, V. et al., *Tet Lett.* 35: 3445 (1994).
Schrader, in *Regulatory Function of Adenosine*; Berne et al., eds. pp. 133–156 (1983).
Sciotti et al., *J. Cerebral Blood Flow Metab.*, 13, 201–207 (1993).
Simmons, H.E. et al., *JACS* 81: 4256 (1959).
Snyder, J.R. et al., *Carbohydrate Res.*, 163, 169–88 (1987).
Srivastava, P.C. et al., *J. Med. Chem.* 18:1237 (1975).
Taylor, E.C. and Hendess, R.W. *J. Am. chem. Soc.*, 87, 1995–2003 (1965).
Tufariello, J. et al. *Tet Lett* 6145 1966).
van der Does, J. *Tet Lett* 27:519 (1986).
Vaughan W.R. et al., *J. Org. Chem.* 26: 138 (1961).
Von E. Doering et al., *JACS* 76, 6162 (1954).
White, *Soc. Neurosci. Abs.*, 20, 308.9 (1994).
Wu, et al., *Cytobios*, 50, 7–12 (1987).
Youssefyeh, R. P. et al., *J. Org. Chem.* 44: 1301 (1979).
Zhang et al., *J. Pharmacol. Exper. Ther.* 264(3), 1415 (1993).
Zoref-Shani et al., *J. Mol. Cell. Cardiol.*, 20, 23–33 (1988).

*Primary Examiner*—James O. Wilson
*Attorney, Agent, or Firm*—Darby & Darby

[57] ABSTRACT

This invention relates to adenosine kinase inhibitors and to nucleoside analogs, C-4' modified pyrrolo[2,3-d]pyrimidine and pyrazolo[3,4-d]pyrimidine nucleoside analogs having activity as adenosine kinase inhibitors. The invention relates to nucleoside analogs of this kind, having zero substitutions or two substitutions at the C-4' position of the furanose (sugar) moiety. The invention also relates to the preparation and use of these adenosine kinase inhibitors in the treatment of cardiovascular, and cerebrovascular diseases, inflammation and other diseases which can be regulated by increasing the local concentration of adenosine.

44 Claims, No Drawings

C-4' MODIFIED ADENOSINE KINASE INHIBITORS

CROSS REFERENCES TO RELATED APPLICATIONS

This application is a continuation in part of Ser. No. 07/812,916, filed Dec. 23, 1991, now abandoned, which is a continuation in part of Ser. No. 07/647,117, filed Jan. 23, 1991, now abandoned, which is a continuation in part 07/466,979, filed Jan. 18, 1990, now abandoned, which is a continuation in part of Ser. No. 07/408,707, filed Sep. 18, 1989, now abandoned. This application is also a continuation in part of Ser. No. 08/191,282, filed Feb. 3, 1994, now U.S. Pat. No. 5,506,347. This disclosures of these applications are incorporated herein by reference.

This invention relates to adenosine kinase inhibitors and to nucleoside analogs, C-4' modified pyrrolo[2,3-d]pyrimidine and pyrazolo[3,4-d]pyrimidine nucleoside analogs having activity as adenosine kinase inhibitors. The invention relates to nucleoside analogs of this kind, having zero substitutions or two substitutions at the C-4' position of the furanose (sugar) moiety. The invention also relates to the preparation and use of these adenosine kinase inhibitors in the treatment of cardiovascular, and cerebrovascular diseases, inflammation and other diseases which can be regulated by increasing the local concentration of adenosine.

BACKGROUND OF THE INVENTION

Adenosine is an endogenously produced molecule that plays a major role in a variety of important cellular processes. It is a vasodilator, can inhibit immune function, enhance activation of mast cells (associated with allergic reactions), inhibit neutrophil oxygen free-radical production, is antiarrhythmic, and is an inhibitory neurotransmitter. Adenosine is phosphorylated to adenosine triphosphate (ATP) which is used by all cells to store energy for use in future energy-utilizing metabolic reactions or mechanical work (e.g. muscle contraction). Extracellular adenosine, frequently prouced by breakdown of intracellular ATP pools, evokes a variety of pharmacological responses through activation of extracellular adenosine receptors located on the surface of nearly all cells. For example, adenosine produces a variety of cardiovascular related effects including vasodilation, inhibition of platelet aggregation, and negative inotropic, chronotropic and domotropic effects on the heart. Adenosine also has effects within the central nervous system (CNS) including inhibition of neurotransmitter release from presynaptic neurons and inhibition of post-synaptic neuron firing in brain and the spinal cord and at sites of inflammation, such as inhibition of neutrophil adhesion to endothelial cells and inhibition of neutrophil oxygen free-radical production.

Compounds that increase extracellular adenosine can be beneficial to living organisms, particularly under certain conditions. For example, compounds that increase adenosine levels have been associated with the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

Adenosine kinase is a cytostolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including pyrrolo[2,3-d]pyrimidine and pyrazolo[3,4-d]pyrimidine analogs have been evaluated for inhibition of adenosine kinase but were reported to have $K_i$'s of greater than 800 nM. Caldwell and Henderson, *Cancer Chemother. Rep.*, 2:237–46 (1971); Miller et al., *J. Biol. Chem.*, 254:2346–52 (1979). A few compounds have been reported as potent inhibitors of adenosine kinase with $K_i$'s of less than 100 nM. These are the purine nucleosides, 5'-amino-5'-deoxyadenosine (Miller et al.) and 1,12-bis(adenosin-$N^6$-yl)dodecane (Prescott et al., *Nucleosides & Nucleotides*, 8:297 (1989)); and the pyrrolopyrimidine nucleosides, 5-iodotubercidin (Henderson et al., *Cancer Chemotherapy Rep. Part 2*, 3:71–85 (1972); Bontemps et al., *Proc. Natl. Acad. Sci. USA*, 80:2829–33 (1983); Davies et al., *Biochem. Pharmacol.*, 35:3021–29 (1986)) and 5'-deoxy-5-iodotubercidin (Davies et al., *Biochem. Pharmacol.*, 33:347–55 (1984) and 35:3021–29 (1986)).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release. Zoref-Shani et al., *J. Mol. Cell. Cardiol.*, 20:23–33 (1988). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release. Schrader in *Regulatory Function of Adenosine*; (Berne et al.) eds. pp. 133–156 (1983). These effects were not apparent in the absence of ADA inhibition, and other studies using isolated rat hearts perfused with 5-iodotubercidin alone, have reported no increase in perfusate adenosine concentration under normoxic conditions Newby et al., *Biochem. J.*, 214:317–323 (1983), or under hypoxic, anoxic or ischemic conditions, Achtenberg et al., *Biochem. J.*, 235:13–17 (1986). In other studies, adenosine release has been measured in neuroblastoma cells in culture and compared with that of a variant deficient in adenosine kinase (AK⁻). The AK⁻ cells used in this study were said to release adenosine at an accelerated rate; the concentration of adenosine in the growth medium was reported to be elevated compared to the normal cells. Green, *J. Supramol. Structure*, 13:175–182 (1980). In rat and guinea pig brain slices, adenosine uptake was reportedly inhibited by the adenosine kinase inhibitors, 5-iodotubercidin and 5'-deoxy-5-iodotubercidin. Davis et al., *Biochem. Pharmacol.*, 33:347–55 (1984). However, inhibition of uptake and intracellular trapping via phosphorylation does not necessarily result in increased extracellular adenosine, since the adenosine could enter other metabolic pathways or the percentage of adenosine being phosphorylated could be insignificant compared to the total adenosine removed.

The effects of adenosine and certain inhibitors of adenosine catabolism, including 5-iodotubericidin were evaluated in an experimental model in which dog hearts were subjected to ischemia and reperfusion; 5-iodotubericidin was reported to have inconsistent effects. Wu, et al., *Cytobios*, 50:7–12 (1987).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The known pyrrolo[2,3-d]pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats. Daves et al., *Biochem. Pharmacol.*, 33:347–55 (1984) and 35:3021–29 (1986); and U.S. Pat. No. 4,455,420). The skeletal muscle effects of these compounds have been poorly documented, while the other effects were considered significant toxicities.

More recent references concerned with the mechanisms and effects of adenosine kinase inhibitors are Keil et al., *Life Sciences* 51:171–76 (1992); Zhang et al., *J. Pharmacol. Exper. Ther.* 264(3): 1415 (1993); Phillis et al., *Life Sciences*, 53: 497–502 (1993); Sciotti et al., *J. Cerebral Blood Flow Metab.*, 13:201–207 (1993); Pak et al., *Soc. for Neuroscience Abs.*, 20: 149.2 (1994); White, *Soc. Neurosci. Abs.*, 20:308.9 (1994); and Firestein et al., *J. Immunology* 154:326–34 (1995). These publications in general show that adenosine kinase inhibitors, as a class, have a role in brain functions, and show promise in connection with the treatment of neurological conditions such as seizures. One reference, Phillis et al., indicates that the known adenosine kinase inhibitor 5-iodotubercidin apparently does not protect against ischemic cerebral injury. Keil et al. disclose that adenosine kinase plays a key role in the mediation of nervous system responses to stimulus, particularly pain (antinociception), but notes that the control of endogenous adenosine concentrations by such means is a complex process requiring further study.

Thus, there is a need for selective, potent, and bioavailable adenosine kinase inhibitors with a useful half-life, i.e. compounds which can be exploited to beneficially influence or control endogenous adenosine kinase activity, and therefore, extracellular adenosine levels. The compounds of the invention are suitable adenosine kinase inhibitors having these characteristics.

SUMMARY OF THE INVENTION

The invention is directed to novel pyrrolo[2,3-d]pyrimidine or pyrazolo[3,4-d]pyrimidine nucleoside analogs having activity as adenosine kinase inhibitors, wherein the furanose moiety has zero substituents or two substituents at the C-4' position. Preferred substitutents are hydroxymethyl, aminomethyl, and methyl. Most preferred are compounds where both substituents are the same, but are not both methyl, or both substituents form a small ring, such as cyclopropyl. In addition to the furanose moiety, additional asymmetric carbons may be present in compounds of the present invention, for example in the substituted heterocyclic pyrrolo[2,3-d]pyrimidine or pyrazolo[3,4-d]pyrimidine ring. All of the resulting isomers, enantiomers, and diastereomers are considered to fall within the scope of the present invention.

These compounds are selective adenosine kinase inhibitors with potencies comparable to or significantly higher than other known adenosine kinase inhibitors. The compounds are also nontoxic, particularly in connection with liver function.

The invention concerns the compounds themselves, the preparation of these compounds, and the in vitro and in vivo adenosine kinase inhibition activity of these compounds. Another aspect of the invention is directed to the clinical use of the compounds to increase adenosine concentrations in biological systems. For example, in vivo inhibition of adenosine kinase prevents phosphorylation of adenosine resulting in higher local concentrations of endogenous adenosine.

The compounds of the invention possess advantages for pharmaceutical use such as enhanced pharmacological selectivity, efficacy, bioavailability, ease of manufacture and compound stability.

The compounds of the invention may be used clinically to treat medical conditions where an increased localized adenosine concentration is beneficial. Accordingly, the invention is directed to the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

Definitions

The following terms generally have the following meanings.

The term "aryl" refers to aromatic groups, which have at least one ring having a conjugated pi electron system, including for example carbocyclic aryl, heterocyclic aryl and biaryl groups, all of which may be optionally substituted. Carbocyclic awl groups are groups wherein all the ring atoms on the aromatic ring are carbon atoms, such as phenyl. Also included are optionally substituted phenyl groups, being preferably phenyl or phenyl substituted by one to three substituents, preferably lower alkyl, hydroxy, lower alkoxy, lower alkanoyloxy, halogen, cyano, perhalo lower alkyl, lower acylamino, lower alkoxycarbonyl, amino, alkylamino, carboxamido, and sulfamido.

Heterocyclic awl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen. Optionally substituted pyridyl represents 2-, 3- or 4-pyridyl or 2-, 3- or 4-pyridyl preferably substituted by lower alkyl or halogen. Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, refer to the groups —NRR' wherein respectively, (a) R is alkyl and R' is hydrogen, aryl or alkyl; (b) R is aryl and R' is hydrogen or aryl, and (c) R is aralkyl and R' is hydrogen or aralkyl.

The term "acylamino" refers to RC(O)NR'.

The term "carbonyl" refers to —C(O)—.

The term "carboxamide" or "carboxamido" refers to —CONR$_2$ wherein each R is independently hydrogen, lower alkyl or lower aryl.

The term "alkyl" refers to saturated aliphatic groups including straight-chain, branched chain and cyclic groups.

The term "alkenyl" refers to unsaturated alkyl groups which contain at least one carbon-carbon double bond and includes straight or branched-chain and cyclic groups.

The term "alkynyl" refers to unsaturated alkyl groups which contain at least one carbon-carbon triple bond and includes straight or branched-chain and cyclic groups.

The term "mercapto" refers to SH or a tautomeric form thereof.

The term "alkylene" refers to a divalent straight chain or branched chain saturated aliphatic radical.

The term "sulfonamido" means —SO$_2$NHR where R is hydrogen or lower alkyl.

The term "N-sulfonyl amine" means —NHSO$_2$R where R is fluoro, lower perfluoroalkyl or lower alkyl.

The term "N-acylated sulfonamide" refers to the group —SO$_2$NHCOR where R is lower alkyl or lower perfluoroalkyl.

The term "basic nitrogen" generally refers to the nitrogen atom of an alkyl amine and implies a compound whose conjugated acid in aqueous solution has a pKa in the range of 9 to 11.

The term "prodrug" refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs fall within the scope of the invention.

The term "pharmaceutically acceptable salt" includes salts of compounds described herein derived from the combination of a compound of this invention and an organic or inorganic acid. The compounds of the present invention are useful in both free base and salt form. In practice the use of salt form amounts to use of base form; both forms are within the scope of the present invention.

The term treatment includes prophylatic or therapeutic administration of compounds of the invention, for the cure or amelioration of disease or symptoms associated with disease, and includes any benefit obtained or derived from the administration of the described compounds.

DETAILED DESCRIPTION OF THE INVENTION

The invention relates to C-4'-modified phenyl pyrrolo[2,3-d]pyrimidine and pyrazolo[3,4-d]pyrimidine nucleoside analogs of Formula 1, having activity as adenosine kinase inhibitors.

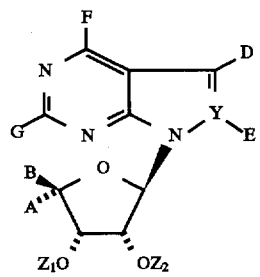

FORMULA 1 wherein:

A and B are both hydrogen, or are each independently alkenyl, the group (CH$_2$)$_n$Q, where n is from 1 to 4 and Q is hydrogen, hydroxy, alkyl, alkoxy, amino, azido, or halogen; or A and B together form a ring of from 3 to 6 carbons, the ring containing 0 to 3 heteroatoms selected from oxygen and nitrogen and optionally substituted by Q as defined above;

D is halogen, aryl, aralkyl, alkynyl, haloalkyl, cyano, carboxamido;

E is nothing when Y is nitrogen; and is hydrogen, halogen, or alkyl when Y is carbon;

F is alkyl, aryl, aralkyl, halogen, amino, alkylamino, arylamino, aralkylamino, alkoxy, aryloxy, aralkyloxy, alkylthio, arylthio, aralkylthio;

G is hydrogen or halogen;

Y is carbon or nitrogen;

Z$_1$ and Z$_2$ are independently hydrogen, acyl, or taken together form a cyclic carbonate; and pharmaceutically acceptable salts thereof.

Preferably, A and B are the same, but are not both methyl, and most preferably are hydrogen or (CH$_2$)$_n$Q where n is 1 and Q is hydroxy, or amino. Also prefered are compounds where A and B form a ring of from 3 to 4 carbons having 0 or 1 heteroatoms. Where A and B are not the same, they are each chosen from the group consisting of methyl, CH$_2$OH, and CH$_2$NH$_2$. Z is preferably hydrogen, or in prodrug form is preferably acyl or carbonate ester.

D is preferably halogen, heterocyclic aryl, phenyl or substituted phenyl;

E is nothing when Y is nitrogen and is preferably hydrogen when Y is carbon;

G is preferably hydrogen; and

F is halogen, amino, arylamino, or heterocyclic arylamino, most preferably phenylamino or substituted phenylamino. Preferred substitutions are halogen, alkyl, alkoxy, or alkylamino or other groups containing a basic or acidic functionality that improves water solubility. The most preferred substitution is at the para position of phenylamino. For example, prefered compounds of the invention include those where F is phenylamino, substituted at the para position with halogen (e.g. fluorine) or a water-solubilizing group.

Exemplary substitutions of the arylamino or phenylamino (Group F) which improve water solubility have the formula (CH$_2$)$_r$T where r is from 0 to 3 and T is an alkyl chain of 0 to 16 carbon atoms containing one or more nitrogen atoms, N-sulfonylated amino, admidoximo, N-aminoguanidino, amidino, guanidino, cyclic derivative of amidino or guanidino, or a 5 or 6 membered alicyclic ring containing nitrogen and optionally one or more oxygen atoms, and optionally substituted by CONVV', where each V is independently an alkyl chain, at least one of which contains one or more basic nitrogen atoms, and optionally oxygen atoms, or V and V' together form a six-membered ring containing at least one basic nitrogen. Similar substitutions can also be made at Group D to improve water solubility.

It will be understood that compounds according to the invention, when made according to the methods set forth below, or by other methods, may be provided in both diastereomeric forms. Usually, one form will predominate in the reaction mixture, however, both forms are within the scope of the invention.

Prodrugs of the compounds of the present invention are included in the scope of this application. Such prodrugs may be prepared by esterification of the hydroxyl groups on the sugar ring. Specially preferred will be the ester derivatives that improve the water solubility properties.

SYNTHESIS OF ADENOSINE KINASE INHIBITORS

The compounds of the invention can be made by several reaction schemes. Exemplary synthetic routes are given below.

The synthesis of compounds of the present invention can be viewed as consisting of the following steps: (A) preparation of the carbohydrate 2, (B) preparation of the heterocycle 3, (C) coupling of the carbohydrate and the heterocycle to provide a protected intermediate 4, (D) modification of substituents on the heterocycle and carbohydrate; and (E) removal of the protecting groups (Scheme 1). Each step is discussed below.

SCHEME 1

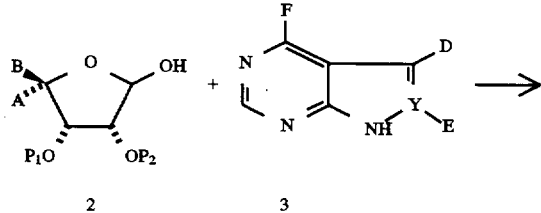

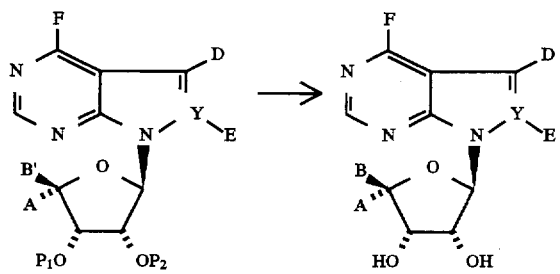

-continued
SCHEME 1

(A) PREPARATION OF THE CARBOHYDRATE 4-substituted carbohydrates of formula 2 are used for the synthesis of compounds of Formula 1, where A and B are chosen from methyl, azidomethyl, aminomethyl, alkylaminomethyl, alkoxymethyl, hydroxymethyl or alkylthiomethyl. The formula 2 carbohydrates are made from the known methyl 2,3-O-methylethylidenefuranoside 5 (Scheme 2). See, Leonard N. J. et al. *J. Heterocycl. Chem.* 3, 485 (1966). The 5-alkoxy group is introduced to 5, to make 6, by the method of Snyder J. R. et al. *Carbohydr. Res.* 163, 169 (1987). The 5-deoxy, azido, amino, alkylamino, alkylthio and alternatively alkoxy carbohydrates are made by first transforming the 5-hydroxy into a leaving group L, preferably mesylate, tosylate, trifluoromethanesulfonate or halide. Treatment of 7 with a nucleophile, e.g. hydride, alkylamine, dialkylamine, alkymercaptan, alcohol or other precursors of amines such as azides or protected amines provides intermediates of formula 8. The isopropylidene is then replaced for less reactive protecting groups, preferably benzyl, according to methods well known to those skilled in the art. For example, Greene T. W., Protective Groups in Organic Chemistry, John Wiley & Sons, New York (1981).

SCHEME 2

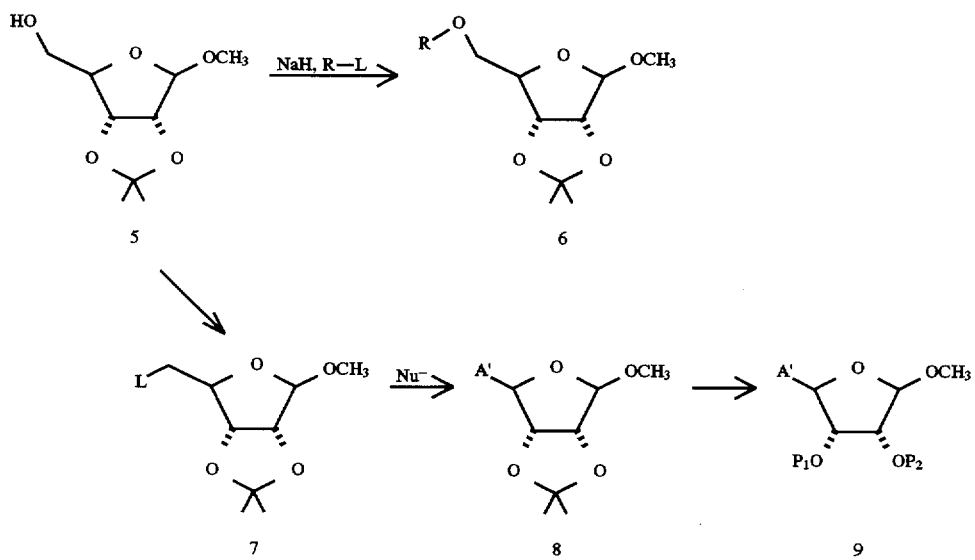

Carbohydrates for compounds of Formula 1 where A is hydroxymethyl are made by the method of Barker R. et al. *J. Org. Chem.* 26, 4605 (1961), to give compounds of formula 9 where A' is preferably benzyl protected hydroxymethyl.

The carbohydrate of Formula 2 is preferably prepared by the method illustrated in Scheme 3. Treatment of methyl glycoside 9 with a thiol or a dithiol, preferably 1,3-propanedithiol, in the presence of an acid or a Lewis acid, preferably boron trifluoride-diethyletherate, gives dithioacetal 10. Oxidation of the generated alcohol by using well described methods and reagents, e.g. pyridinium dichromate, pyridinium chlorochromate, Moffat oxidation, sulfur trioxide-pyridine, preferably Swern oxidation, gives ketone 11. Chelation-controlled addition of an organometallic B'—M, preferably organolithium, stereoselectively provides tertiary alcohol 12. The dithioacetal protecting group is removed using a modification of the procedure developed by Fetizon M. et al. *J. Chem. Soc. Chem. Comm.* 382 (1972), involving treatment of thioacetal with iodomethane and an inorganic base, preferably calcium carbonate. Alternatively, other dithioacetal deprotection procedures are known which use reagents such as N-halosuccinimide, cupric, mercuric and silver salts. However the use of these oxidative procedures is precluded for compounds bearing incompatible functional groups such as thioethers, azides or amines.

SCHEME 3

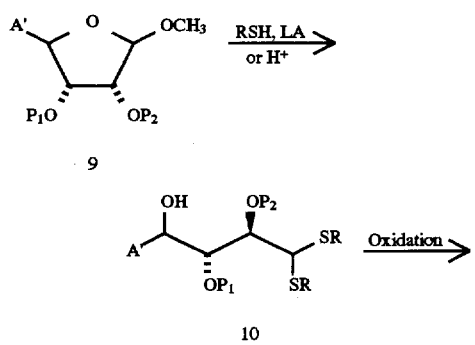

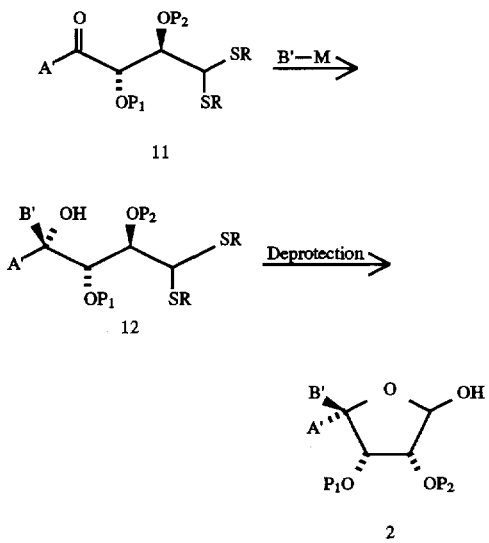

Alternatively the second 4-C-substituent may be introduced using the procedure of Youssefyeh R. D. et al. *J. Org Chem.* 44(8), 1301(1979) where alkylation of an aldehyde of formula 15 with electrophile B'+ followed by a reduction gives compound 16 (Scheme 4). The aldehyde is obtained from the oxidative cleavage, preferably with sodium periodate, of hexofuranose 13 or oxidation of the primary alcohol of furanoside 14, preferably using a Moffat oxidation. Another method to obtain compounds of formula (16) is to use the procedure of Johnson C. R. et al. *J. Org Chem.* 59(20), 5854 (1994).

SCHEME 4

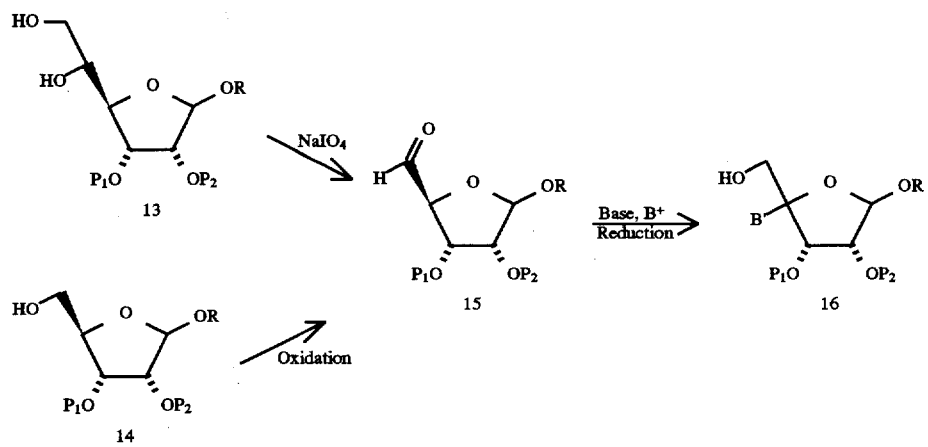

Carbohydrates for compounds of Formula 1 where A=B=H are made using a suitably protected carbohydrate of formula 2 where A'=B'=H. This carbohydrate is easily obtained from erythrofuranose according to methods well known to those skilled in the art described in Greene T. W., *Protective Groups in Organic Chemistry*, John Wiley & Sons, New York (1981).

Carbohydrates of formula 2, where A and B form a ring, e.g. cyclopropyl, are prepared from D-ribose via the well known enol ether 17 (Scheme 5). Inokawa S. et al. *Carbohydr. Res.* 30, 127 (1973). Cyclopropanation is performed according to the procedure of Simmons H. E. et al. *J. Am Chem. Soc.* 81, 4256 (1959) or one of its many modifications. Alternatively cyclopropanation is accomplished with a diazoalkane and a metal salt, preferably palladium. Cossy J. et al. *Tetrahedron Lett.* 28(39), 4547 (1987).

SCHEME 5

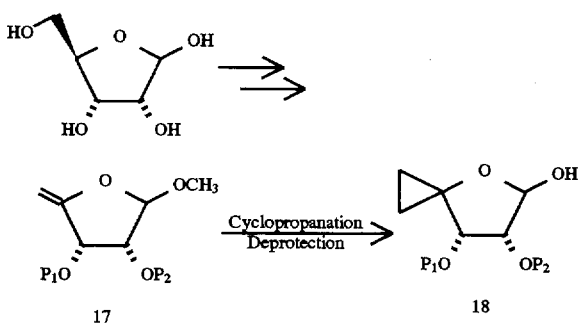

Another alternative is to generate a carbene from a dihaloalkane or trihalomethane with a base in the presence of the olefin (Von E. Doering W. et al. *J. Am. Chem. Soc.* 76, 6162 (1954)) followed by dehalogenation, for example according to Jefford C. W. et al. *J. Am. Chem. Soc.* 94, 8905 (1972). Cycloaddition between diazomethane and compounds of formula 17 provides a pyrazoline intermediate which upon photolysis and deprotection produces spirocyclopropane 18 (Samano V. et al. *Tetrahedron Lett.* 35(21), 3445 (1994)). The deprotection of the anomeric center is in turn accomplished using one of the many procedures well known to those skilled in the art, e.g. Greene, T. W., *Protective Groups in Organic Chemistry*, John Wiley & Sons, New York, (1981).

Carbohydrates of formula 20 are made by a wide variety of procedures. Reaction of olefin 17 with ketene under the conditions of Redlich H. et al. *Angew. Chem.* 101(6), 764 (1989) gives cyclobutanone 19 (Scheme 6), with is then deoxygenated using the procedure of Mori K. et al. *Tetrahedron*, 43(10), 2229 (1987) or Romming C. et al. *Acta Chem. Scan. B*, 40(6), 434 (1986). The free reducing sugar is then obtained as mentioned above (Greene T. W. *Protective Groups in Organic Chemistry* John Wiley & Sons, New York, 1981).

SCHEME 6

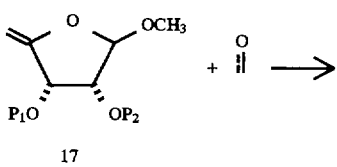

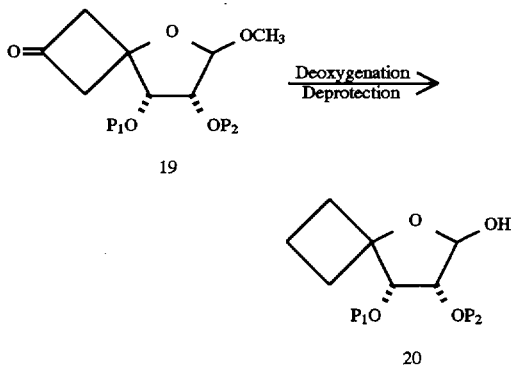

An alternative route uses the photochemical cyclization of a carbohydrate of formula 22 to give cyclobutanol 23 (Scheme 7, Paquette L. A. et al. *J. Am. Chem. Soc.* 108(13), 3841 (1986). Deoxygenation of alcohol 23 occurs according to the procedure of Barton D. H. R. et al. *Pure Appl. Chem.* 53, 15 (1981). Precursor 22 is made by 4-alkylation of the corresponding aldehyde derived from selectively protected methyl riboside 21, e.g. Youssefyeh R. D. et al. *J. Org Chem.* 44(8), 1301 (1979).

SCHEME 7

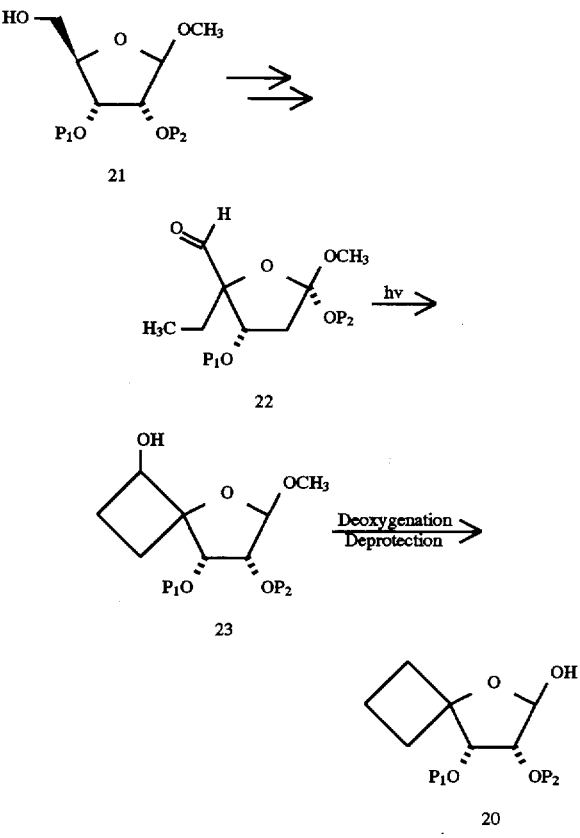

Alkylation of aldehyde 15 with a two carbon dielectrophile, preferably diiodoethane, gives 4-disubstituted aldehyde 24 (Scheme 8, Youssefyeh R. D. et al. *J. Org Chem.* 44(8), 1301 (1979)). Treatment of aldehyde 24 with a metal or metal salt, preferably samarium diiodide (Molander G. A. et al. *J. Am. Chem. Soc.* 109(2), 453 (1987)), or with an organometallic reagent, preferably an alkyllithium (Vanderdoes T. et al. *Tetrahedron Lett.* 27(4), 519 (1986)), achieves the ring closure. The cyclobutanol is then deoxygenated and deprotected at the anomeric position using the procedures previously mentioned to provide spirocyclobutylfuranose 20.

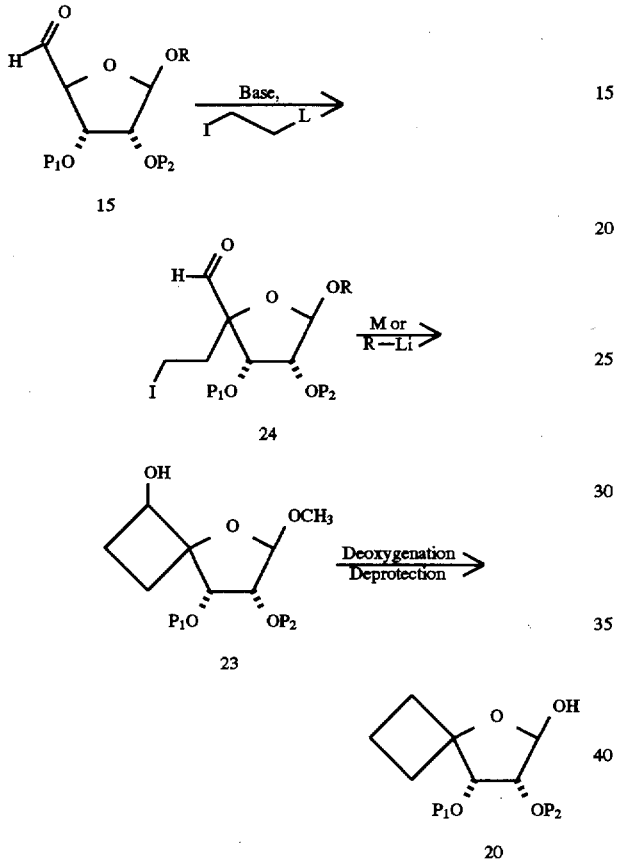

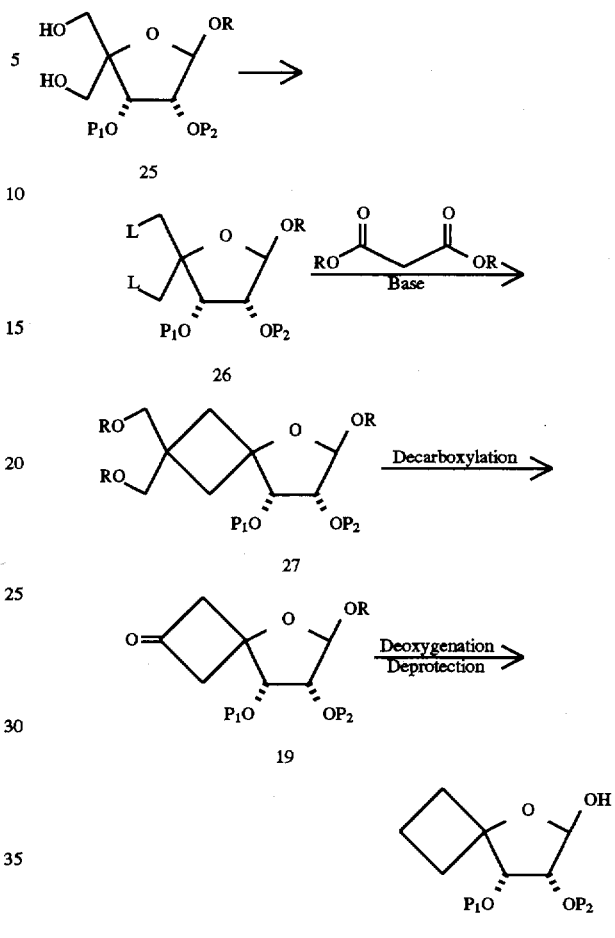

An alternative method to make carbohydrate of formula 20 is illustrated in Scheme 9. Activation of the two primary hydroxyl groups using the many procedures well known to those skilled in the art (Larock R. C. *Comprehensive Organic Transformations*, VCH Publishers, Inc. New York (1989)) followed by dialkylation with a malonate produces dicarboxylate spirocyclobutane 27 (Pecquet P. et al. *Heterocycles* 34(4), 739 (1992)). Decarboxylation using the procedure of Tufariello J. J. et al. *Tetrahedron Lett.* 6145 (1966) followed by deoxygenation and deprotection of cyclobutanone 19 as previously mentioned gives spirocyclobutane 20.

Carbohydrate of formula 29 is made by activation of one of the primary hydroxyl groups of diol 25 (Scheme 10, Larock R. C. *Comprehensive Organic Transformations*, VCH Publishers, Inc. New York, (1989)). Cyclization occurs upon treatment of alcohol 28 with a base (Koll P. et al. *Angew. Chem. Int. Ed. Engl.* 25, 368 (1986)). The anomeric position is then deprotected as previously mentioned to afford spirooxetanofuranose 29.

Alternatively, compound 29 is obtained via Mitsunobu reaction of diol 25 under the conditions of Berkowitz W. F. et al. *J. Org. Chem.* 52(6), 1119 (1987) which gives compound 29 after deprotection. As another alternative, lithium chloride treatment of a cyclic carbonate derived from diol 25 followed by deprotection also gives carbohydrate 29.

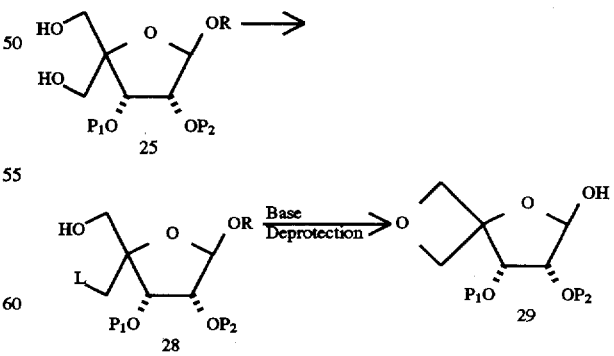

The syntheses of the carbohydrates of formula 32 are illustrated in Schemes 11, 12 and 13. Treatment of activated carbohydrate 31 with a base prior to deprotection gives spiroazetidinofuranose 32 (Scheme 11, Vaughan W. R. et al.

J. Org. Chem. 26, 138 (1961)). Aminoalcohol 30 is prepared following the procedures used to make carbohydrates of formula 2 (Scheme 3).

SCHEME 11

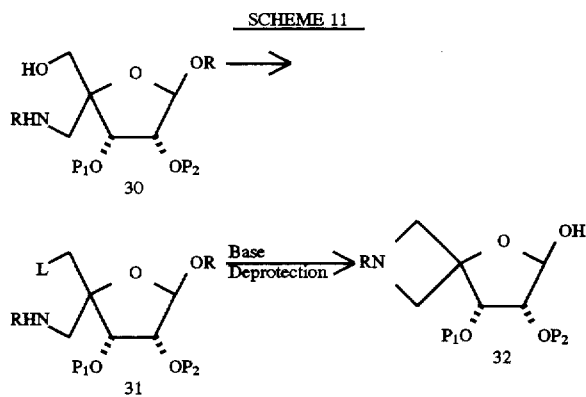

Alternatively, treatment of diactivated compound 26 with ammonia, a primary amine, a protected amine or an activated amine (Scheme 12) followed by deprotection gives carbohydrate 32. See, Juaristi E. et al. Tetrahedron Lett. 25(33), 3521 (1984).

SCHEME 12

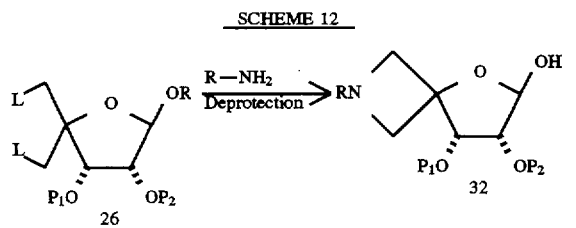

An other alternative is to treat azidoalcohol 33 with a trialkyl or triaryl phosphine (Scheme 13, Szmuszkovicz J. et al. J. Org. Chem. 46(17), 3562 (1981)). Decomposition of the azido group and Mitsunobu like cyclization gives after deprotection azetidine 32.

SCHEME 13

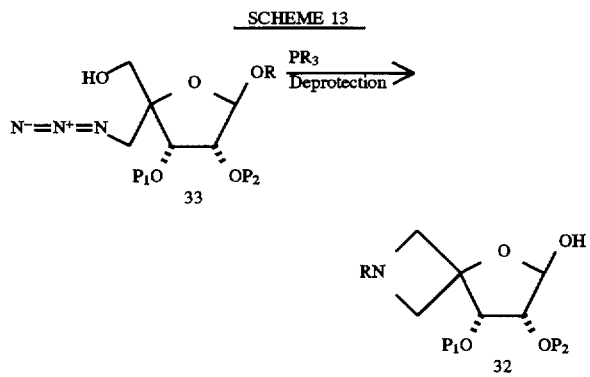

(B) PREPARATION OF THE HETEROCYCLE

Heterocycles for compounds of formula 1 (Scheme 1) where Y=C, F' and D' are substituted aromatic groups, preferably para-fluorophenyl, G is hydrogen, and E' is a hydrogen, alkyl, preferably hydrogen, are made via a pyrrole intermediate 37 made using the procedure of Gewald, K. Z. Chem., 1, 349 (1961). Alternatively, 37 is made by condensing phenone 34, where L is halide or sulfonate, is treated with phthalimide 35 in order to introduce the pyrrole nitrogen. Knoevenagel condensation of ketone 36 with malonitrile followed by removal of the phthalimide protecting group affords pyrrole 37. 349.

Upon treatment with an orthoester, preferably triethylorthoformate, an imidate is formed which is further condensed with a substituted aniline, preferably para-fluroaniline, to give diaryl-pyrrolopyrimidine 39 (Taylor, E. C. et al. J. Am Chem. Soc. 87(9),1995 (1965)). Additionally, the pyrrolopyrimidine can be further functionalized at the 6 position, when E' is methyl, by treatment with N-bromosuccinimide (Saroja, B. et al. Tetrahedron Lett 1984, 25(47), 5429). Treatment of this bromomethylene with a nucleophile or with an alkyllithium and an electrophile allows easy introduction of functional groups such as amino or guanidino.

SCHEME 14

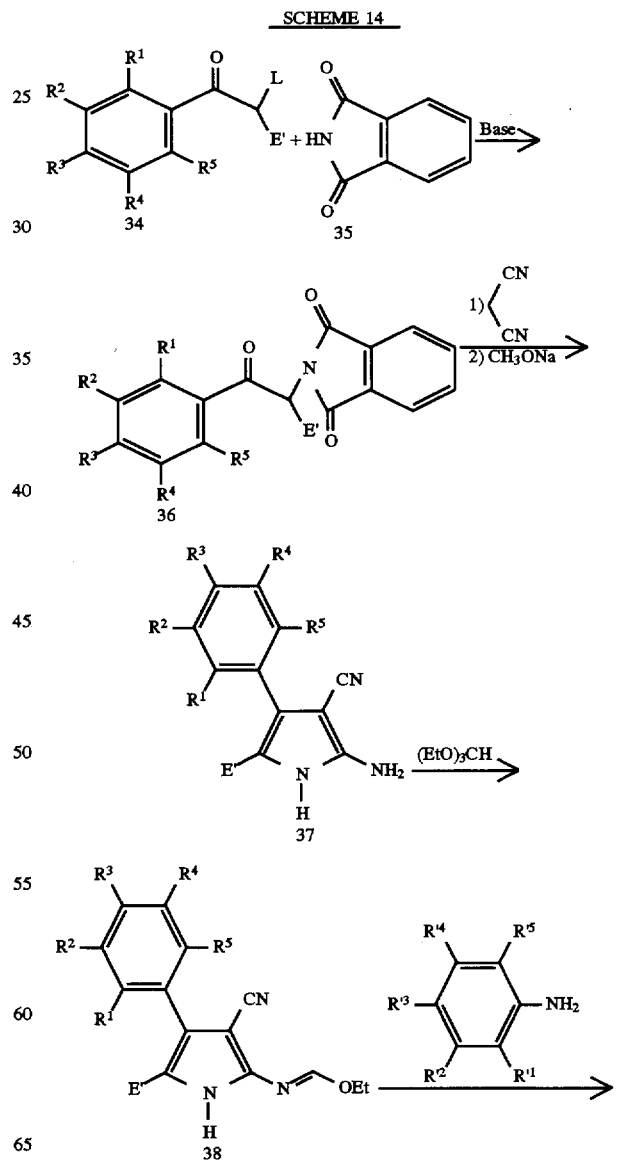

-continued
SCHEME 14

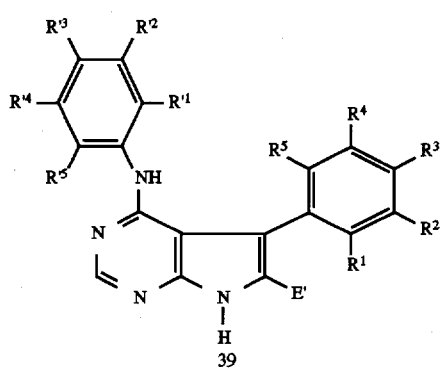

Heterocycles for compounds of formula 1 (Scheme 1) where Y=N, F' and D' are substituted aromatic groups, preferably para-fluorophenyl.

SCHEME 15

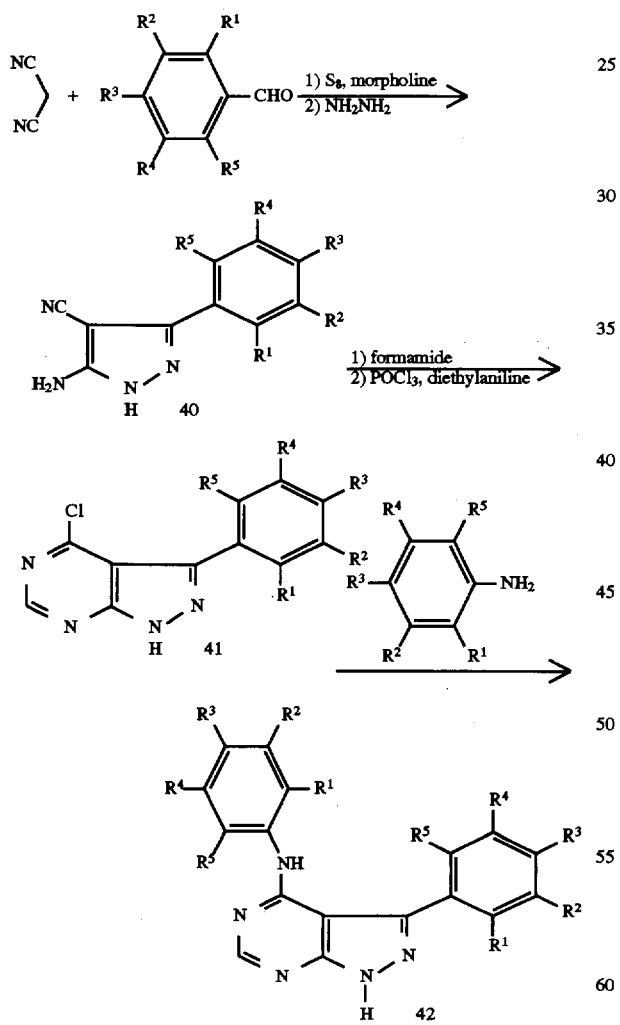

Compounds where E is "nothing" are made using the procedure of Kobayashi, S. *Chem. Pharm. Bull.* (Japan) 21, 941 (1973). Knoevenagel condensation of malonitrile with a substituted benzaldehyde, preferably para-fluorobenzaldehyde, followed by treatment with hydrazine gives 5-aminopyrazole-4-carbonitrile 40 (Scheme. 15). The 4-chloropyrazolo[3,4-d]pyrimidine 41 is obtained upon ring closure reaction with formamide and chlorination using the procedure described by Cheng, C. C. *J. Org. Chem.* 21, 1240 (1966). Treatment of chloride 41 with ammonia, for the 4-amino series, or a substituted aniline preferably para-fluoroaniline, as previously mentioned gives diarylpyrazolopyrimidine 42.

C. COUPLING OF THE CARBOHYDRATE WITH THE HETEROCYCLE

The coupling of the carbohydrate 2 with pyrrolo[2,3-d] pyrimidine heterocycles is accomplished as follows (Scheme 16). The sugar is first converted to its 1-halo derivative, preferably chloro, by reacting it with $CCl_4$ and HMPT by a procedure described in Wilcox, C. T. et al. *Tetrahedron Lett.* 27(9), 1011 (1986). The halo derivative is condensed with the anion of the heterocycle 3 (where Y is carbon and E is hydrogen) using a phase transfer catalyst such as TDA-1. Rosemeyer H., and Seela, F., *Helvetica Chimica Acta*, 71:1573 (1988). The resulting blocked nucleosides are deprotected by a variety of procedures well known to those skilled in the art.

SCHEME 16

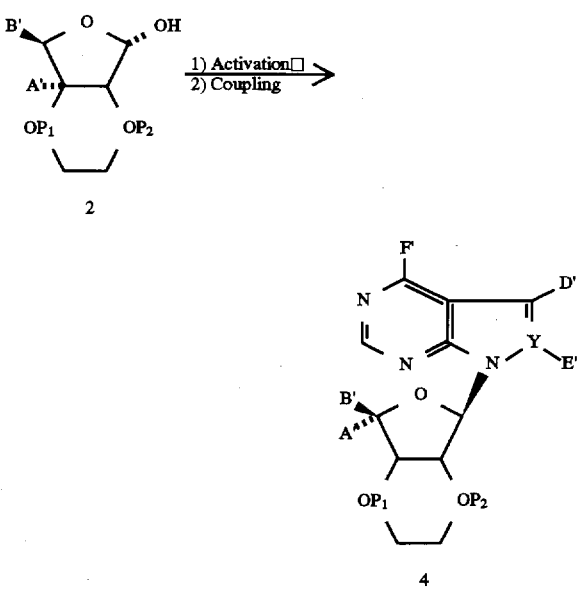

Coupling of sugars to the pyrazzolo[3,4-d]pyrimidine bases is performed by Lewis acid catalysis conditions. Cottom, et al., *J. Med. Chem.*, 27, 11210 (1984). In such cases the sugars are converted to their 1-O-acyl form, preferably 1-O-acetyl, by again using one of the many standard acetylation procedures. A mixture of the heterocycle 3 (where Y is nitrogen) and the acetylated sugar in boiling nitromethane is treated with $BF_3$-etherate. the products are purified by chromatography or crystallization, and are deprotected to obtain the final compounds.

D. MODIFICATION OF SUBSTITUENTS ON THE HETEROCYCLE

Due to the chemical incompatibility between some of the substituents on the heterocycle and the glycosidation-reaction conditions, the final functionalization of the nucleoside is done after the coupling reaction. For example, the 5-aryl group is introduced onto the pyrrolopyrimidine ring system using one of the many palladium-catalyzed cross coupling procedures (review: Stille, J. K. *Ang. Chem., Int. Ed. Engl.* 25, 508(1986)).

Typically, a 4-substituted-amino-5-halopyrrolo[2,3-d] pyrimidine 44, where the halogen is iodo, is coupled to an arylboronic acid (i.e. A=B(OH)$_2$ in Scheme 17) in the presence of a catalyst such as tetrakistriphenylphosphine palladium.

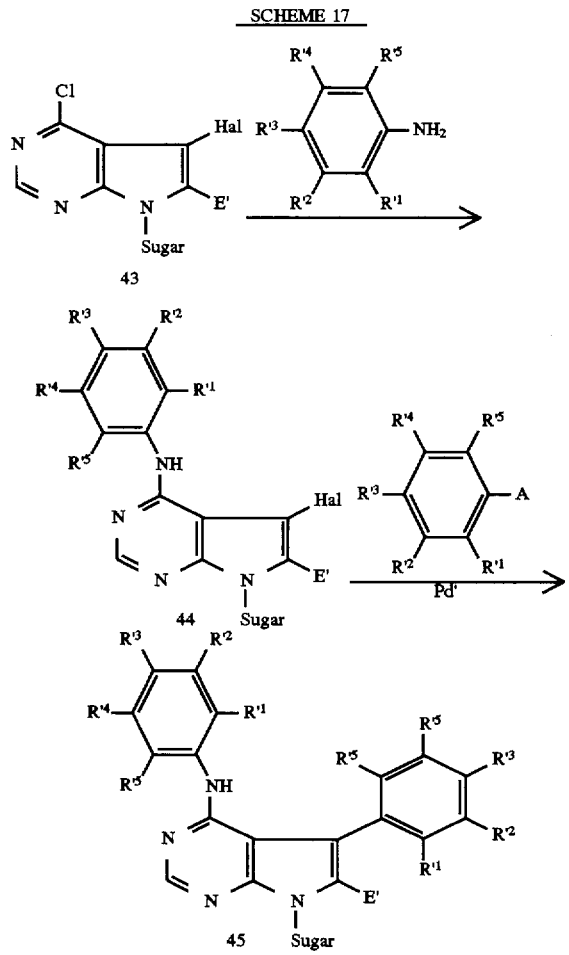

Alternatively, in place of aryl boronic acids, other activated aryl compounds such as aryltrialkyltin(A=Sn(alkyl)$_3$ is successfully used to obtain the final product 45.

Further modifications can be added to the aromatic rings after cross coupling with the heterocycle either before or after glycosidation. Reduction, oxidation and/or deprotection steps are done at this stage. For instance a cyano group is oxidized to its carboxamide or reduced to its amine. A N-phenylacetamide is deprotected and kept as its aniline or transformed to its trifluoromethanesulfonamide to improve water solubility.

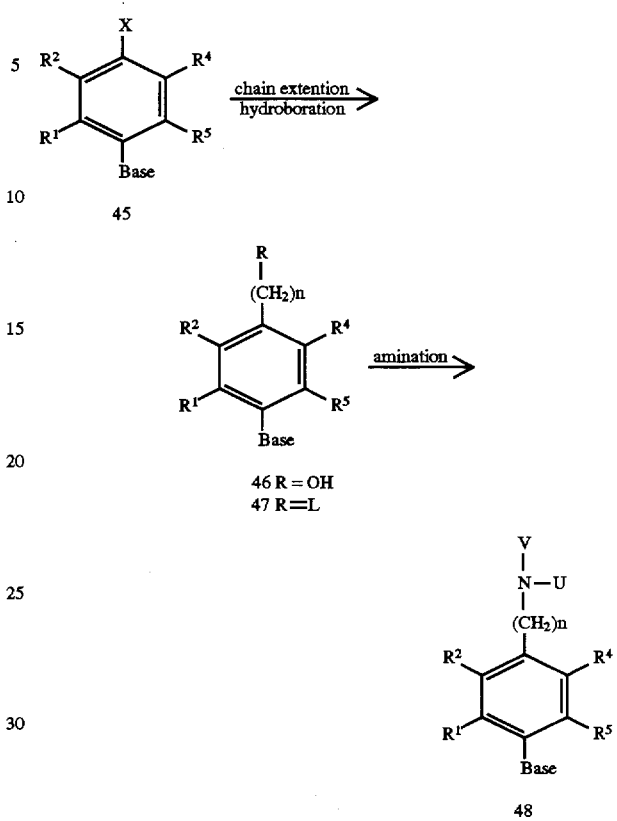

Carbon chain extension is done at this stage (Scheme 18). The aromatic ring substituent on the glycosilated intermediate 45 where X is halide or trifluoromethanesulfonate is coupled with a vinyl or allyl trialkyltin species using one of the many palladium-catalyzed cross coupling procedures (review: Stille, supra). The double bond is then oxygenated at the terminal position and the resulting alcohol 46 is converted to a leaving group L, preferably iodide (Srivastava, P. C. et al. *J. Med Chem.* 1975, 18(12), 1237). Displacement by an amine completes the carbon chain extension and improves the water solubility for compounds of formula 48.

E. REMOVAL OF THE PROTECTING GROUPS

Acid labile protecting groups such as ketals, silyl ethers or ethers are removed using a dilute acid or a weak organic acid, e.g. 0.1N hydrochloric acid or 70% aqueous trifluoroacetic acid (Greene, T. W., Protective Groups in Organic Chemistry, John Wiley & Sons, New York (1981). Base labile protecting groups such as acyls or carbamates are removed by treatment with an organic or inorganic base, e.g. sodium methoxide, sodium hydroxide, ammonia (Id). Benzyl protecting groups are removed by hydrogenolysis in the presence of a metal catalyst, preferably palladium chloride. Shen, T. Y. et al *J. Org. Chem.* 30, 835 (1965).

Preferred compounds of the invention, which can be made using the methods described, include the following.

EXAMPLES

Example 1

Preparation of compound of formula 10
2,3,5-tri-O-(phenylmethyl)-1-(1,3-dithian-2-yl)-D-ribo-pentane Boron trifluoride diethyl etherate (11.4 mL, 92.4 mmol) was added to a solution of methyl 2,3,5-tri-O-

(phenylmethyl)-D-ribofuranoside (30 g, 66 mmol) (Barker, R. and Fletcher, H. G. *J. Org. Chem.* 1961, 26, 4605) and 1,3-propanedithiol (10 mL, 99 mmol) in dry dichloromethane (130 mL) at −48° C. The reaction mixture was stirred 30 minutes at −48° C. and warmed to room temperature in the course of one hour. After stirring at room temperature for one hour, the mixture was quenched with saturated aqueous sodium bicarbonate, diluted with ethyl acetate and washed with saturated aqueous sodium bicarbonate and saturated aqueous sodium chloride. The organic layer was dried over sodium sulfate and concentrated under reduced pressure. The residue was purified by flash chromatography on silica gel (hexanes/ethyl acetate 90/10 to 75/25). Yield 31.9 g, 94%, Rf=0.3 (silica gel, hexanes/ethyl acetate 80/20).

Example 2

Preparation of compound of formula 11

3S,4R)-1,3,4-tri[(phenylmethyl)oxy]-5-(1,3-dithian-2-yl)pentan-2-one

A solution of dimethyl sulfoxide (22.1 mL, 312 mmol) in dry dichloromethane (100 mL) was added dropwise over 10 minutes to a solution of oxalyl chloride (16.3 mL, 187 mmol) in dry dichloromethane (200 mL) at −78° C. After stirring 10 minutes at −78° C., a solution of the compound of Example 1 (31.9 g, 62.4 mmol) in dry dichloromethane (100 mL) was added dropwise to the reaction mixture over 20 minutes at −78° C. After stirring at −78° C. for 20 minutes, a solution of triethylamine (87 mL, 624 mmol) in dry dichloromethane (100 mL) was added dropwise over 10 minutes at −78° C. After completion of the addition the internal temperature was allowed to raise to −40° C. over 30 minutes. The reaction mixture was quenched with saturated aqueous ammonium chloride and warmed to room temperature. The layers were separated and the aqueous layer was back extracted twice with dichloromethane. The combined organic extracts were dried over sodium sulfate and concentrated under reduced pressure. The residue was purified by flash chromatography on silica gel (hexanes/ethyl acetate 90/10 to 70/30). Yield: 27.9 g, 88%, Rf=0.35 (silica gel, hexanes/ethyl acetate 80/20).

Example 3

Preparation of compound of formula 12

4-C-[(phenylmethyl)oxy]methyl-2,3,5-tri-O-phenylmethyl-1(1,3-dithian-2-yl)-D-ribo-pentane A solution of the compound of Example 2 (1 g, 1.97 mmol) in dry tetrahydrofuran (25 mL) was added dropwise over 5 minutes to a solution of [(phenylmethyl)oxy]methyllithium (3.94 mmol) (Still, W. C. *J. Am. Chem. Soc.* 1978, 100, 1481) in dry tetrahydrofuran (25 mL) at −78° C. After stirring for 20 minutes at −78° C., the reaction mixture was quenched with saturated aqueous ammonium chloride, warmed to room temperature, diluted with ethyl acetate and washed with saturated aqueous ammonium chloride. The organic layer was dried over sodium sulfate and concentrated under reduced pressure. The residue was purified by flash chromatography on silica gel (hexanes/ethyl acetate 90/10 to 75/25). Yield: 1.05 g, 85%, Rf=0.45 (silica gel, hexanes/ethyl acetate 70/30).

Example 4

Preparation of compound of formula 2

4-C-[(phenylmethyl)oxy]methyl-2,3,5-tri-O-(phenylmethyl)-D-ribofuranose

A heterogeneous mixture of calcium carbonate (4 g, 40 mmol), iodomethane (1.25 mL, 20 mmol) and the compound of Example 3 (2.52 g, 4 mmol) in acetonitrile/tetrahydrofuran/water (1/1/9, 44 mL) was refluxed overnight (Fetizon, M. *J. Chem. Soc., Chem. Comm.* 1972, 382). More iodomethane (1.25 mL, 20 mmol) was added and refluxing was pursued for 24 hours. The mixture was cooled, diluted with ethyl acetate and washed with saturated aqueous sodium chloride. The aqueous layer was extracted with dichloromethane and the combined organic extracts were dried over sodium sulfate and concentrated under reduced pressure. The residue was purified by flash chromatography on silica gel (hexanes/ethyl acetate 80/20 to 65/35). Yield: 2.06 g, 95%, Rf=0.2 (silica gel, hexanes/ethyl acetate 70/30).

Example 5

Preparation of compound of formula 4

4-N-phenylamino-5-phenyl-7-(4-C-[(phenylmethyl)oxy]methyl-2,3,5-tri-O-(phenylmethyl)-β-D-ribofuranosyl)pyrrolo[2,3-d]pyrimidine Hexamethylphosphorous triamide (415 μL, 1.95 mmol) was added to a solution of carbon tetrachloride (250 μL, 2.6 mmol) and lactol 5 (349 mg, 0.65 mmol) in dry toluene at −78° C. The reaction mixture was warmed to 0° C. in the course of one hour and stirred at 0° C. for 30 minutes. The orange solution was quenched with water, diluted with toluene and washed with water and saturated aqueous sodium chloride. The organic layer was dried over sodium sulfate and concentrated under reduced pressure to a volume of c.a. 5 mL. The chloro-sugar solution was added to a mixture of 4-phenylamino-5-phenyl-pyrrolo[2,3-d] pyrimidine (370 mg, 1.3 mmol), finely powdered potassium hydroxide (85%, 170 mg, 2.6 mmol), Tris[2-(2-methoxyethoxy)ethyl]amine (420 μL, 1.3 mmol) and 4 Å molecular sieves in dry toluene which had been stirring at room temperature for 2 hours. After stirring overnight at room temperature, the reaction mixture was filtered through Celite® and the filtering pad was rinsed with ethyl acetate. The filtrate was diluted with ethyl acetate and washed with saturated aqueous sodium chloride. The organic layer was dried over sodium sulfate and concentrated under reduced pressure. The residue was purified by flash chromatography on silica gel (hexanes/ethyl acetate 90/10 to 70/30). Yield: 229 mg, 44%, Rf=0.6 (silica gel, hexanes/ethyl acetate 80/20).

Example 6

Preparation of compound of formula 1

4-N-phenylamino-5-phenyl-7-(4-C-hydroxymethyl-β-D-ribofuranosyl)pyrrolo[2,3-d]pyrimidine A mixture of palladium hydroxide (200 mg) and 4-N-phenylamino-5-phenyl-7-(4-C-[(phenylmethyl)oxy]methyl-2,3,5-tri-O-(phenylmethyl)-β-D-ribofuranosyl)pyrrolo[2,3-d]pyrimidine (212 mg, 0.26 mmol) in acetic acid/methanol (1/1, 10 mL) was vigorously stirred at room temperature under one atmosphere of hydrogen. After 7 days of stirring the reaction mixture was filtered through Celite® and the filtering pad was rinsed with hot methanol. The filtrate was concentrated under reduced pressure and the solid residue was recrystallized from ethanol. Yield: 30 mg, 25%, Rf=0.4 (silica gel, dichloromethane/methanol 80/20), mp 232° C.

Example 7

Preparation of compound of formula 10

5-deoxy-2,3-di-O-(phenylmethyl)-1-(1,3-dithian-2-yl)-D-ribo-pentane

The title compound was synthesized following a procedure analogous to the synthesis described in Example 1.

Thus methyl 5-deoxy-2,3-di-O-(phenylmethyl)-D-ribofuranoside (7 g, 21.3 mmol) gave 7.9 g, 92%, Rf=0.35 (silica gel, hexanes/ethyl acetate 70/30).

Example 8

Preparation of compound of formula 11

(3S,4R)-3,4-bis-[(phenylmethyl)oxy]-5-(1,3-dithian-2-yl)pentan-2-one

The title compound was synthesized following a procedure analogous to the synthesis described in Example 2. Thus the compound of Example 7 (7.9 g, 19.5 mmol) gave 6.32 g, 80%, Rf=0.2 (silica gel, hexanes/ethyl acetate 70/30).

Example 9

Preparation of compound of formula 12

5-deoxy-4-C-methyl-2,3-di-O-(phenylmethyl-1-(1,3-dithian-2-yl)-D-ribo-pentane

A solution of the compound of Example 8 (2 g, 5 mmol) in dry tetrahydrofuran (30 mL) was added dropwise over 10 minutes to a solution of methyllithium (20 mmol) in dry tetrahydrofuran (20 mL) at –78° C. After stirring for 20 minutes at –78° C., the reaction mixture was quenched by slow addition of a solution of acetic acid (2 mL) in dry tetrahydrofuran (10 mL) over 5 minutes at –78° C. The quenched solution was warmed to room temperature, diluted with ethyl acetate and washed with saturated aqueous sodium bicarbonate and saturated aqueous sodium chloride. The organic layer was dried over sodium sulfate and concentrated under reduced pressure. The residue was purified by flash chromatography on silica gel (hexanes/ethyl acetate 85/15 to 75/25). Yield: 2.038 g, 98%, Rf=0.38 (silica gel, hexanes/ethyl acetate 70/30).

Example 10

Preparation of compound of formula 2

5-deoxy-4-C-methyl-2-3-di-O-(phenylmethyl)-D-ribofuranose

The title compound was synthesized following a procedure analogous to the synthesis described in Example 4. Thus, the compound of Example 9 (2.04 g, 4.87 mmol) gave 1.4 g, 88%, Rf=0.4 (silica gel, hexanes/ethyl acetate 70/30).

Example 11

Preparation of compound of formula 2

5-deoxy-4-C-methyl-2,3-O-(methylethylidene)-D-ribofuranose

A mixture of palladium hydroxide (0.5 g) and the compound of Example 10 (2.62 g, 7.98 mmol) was vigorously stirred at room temperature for 3 hours under one atmosphere of hydrogen. The reaction mixture was filtered through Celite® and the filtering pad was rinsed with hot methanol. The filtrate was concentrated under reduced pressure and methylformamide dimethylformamide. The residue was dissolved in dimethylformamide (10 mL). p-Toluenesulfonic acid monohydrate (catalytic) and 2,2-dimethoxypropane (4.6 mL, 32 mmol) were added. After stirring overnight at room temperature, the reaction mixture was diluted with ethyl acetate and washed with saturated aqueous sodium bicarbonate and saturated aqueous sodium chloride. The organic layer was dried over sodium sulfate and concentrated under reduced pressure. The residue was purified by flash chromatography on silica gel (hexanes/ethyl acetate 80/20 to 70/30). Yield: 507 mg, 34%, Rf=0.3 (silica gel, hexanes/ethyl acetate 70/30).

Example 12

Preparation of compound of formula 4

4-phenylamino-5-phenyl-7-(5-deoxy-4-C-methyl-2,3-O-(methylethylidene)-β-D-ribofuranosyl)pyrrolo-[2,3-d]pyrimidine Hexamethylphosphorous triamide (800 μL, 4.35 mmol) was added to a solution of carbon tetrachloride (600 μL, 5.8 mmol) and the compound of example 11 (272 mg, 1.45 mmol) in dry toluene at –50° C. The reaction mixture was warmed to –10° C. in the course of 30 minutes and stirred at –10° C. for 15 minutes. The orange solution was quenched with water, diluted with toluene and washed with water and saturated aqueous sodium chloride. The organic layer was dried over sodium sulfate and concentrated under reduced pressure to a volume of c.a. 5 mL. The chloro-sugar solution was added to a mixture of 4-phenylamino-5-phenyl-pyrrolo[2,3-d]pyrimidine (830 mg, 2.9 mmol), finely powdered potassium hydroxide (85%, 380 mg, 5.8 mmol) and Tris[2-(2-methoxyethoxy)ethyl]amine (925 μL, 2.9 mmol) in dry toluene which had been stirring at room temperature for 90 minutes. After stirring overnight at room temperature, the reaction mixture was diluted with ethyl acetate and washed with saturated aqueous ammonium chloride. The organic layer was dried over sodium sulfate and concentrated under reduced pressure. The residue was purified by flash chromatography on silica gel (hexanes/ethyl acetate 70/30 to 50/50). Yield: 223 mg, 34%, Rf=0.3 (silica gel, hexanes/ethyl acetate 60/40).

Example 13

Preparation of compound of formula 1

4-N-phenylamino-5-phenyl-7-(5-deoxy-4-C-methyl-β-D-ribofuranosyl)pyrrolo[2,3-d]pyrimidine A solution of 4-phenylamino-5-phenyl-7-(5-deoxy-4-C-methyl-2,3-O-(methylethylidene)-β-D-ribofuranosyl) pyrrolo[2,3-d]pyrimidine (220 mg) in 70% aqueous trifluoroacetic acid (20 mL) was stirred at 0° C. for one hour and at room temperature for one hour. The reaction mixture was concentrated under reduced pressure and azeotroped twice with water and twice with ethanol. The residue was neutralized with saturated aqueous sodium bicarbonate and the precipitated nucleoside was filtered and rinsed with water. The solid was recovered and recrystallized from ethanol. Yield: 130 mg, 65%, Rf=0.5 (silica gel, dichloromethane/methanol 90/10), mp 198°–200° C.

Example 14

Preparation of methyl 2,3-O-(methylethylidene)-4-spirocyclopropyl-D-erythro-furanoside A solution of methyl 5-deoxy-2,3-O-(methylethylidene)-β-D-pent-erytho-furanoside (2 g, 10.7 mmol) (Inokawa, S. et al. *Carboghyd. Res.* 1973, 30, 127) and diodomethane in dry ether (20 mL) was added dropwise over 4 hours to a refluxing suspension of freshly made zinc-copper couple in dry ether. The reaction mixture was refluxed overnight, cooled, diluted with ether and washed with saturated aqueous ammonium chloride. The organic layer was dried over sodium sulfate and concentrated under reduced pressure. The residue was purified by flash chromatography on silica gel (pentane/ether 90/10 to 80/20) to provide the title compound 18 (1 g, 47%), Rf=0.3 (silica gel, hexanes/ethyl acetate 90/10).

Example 15

Preparation of compound of formula 18

2,3-O-(methylethylidene)-4-spirocyclopropyl-D-erythro-furanose

A mixture of methyl 2,3-O-(methylethylidene)-4-spirocyclopropyl-D-erythro-furanoside (2.57 g, 12.8 mmol), 1N aqueous hydrochloric acid (20 mL) and tetrahydrofuran (20 mL) was refluxed for 1 hour. The cooled reaction mixture was neutralized with DOWEX® 1 X8-200 ion exchange resin (OH⁻ form), filtered and rinsed with methanol. The combined filtrates were concentrated under reduced pressure and azeotroped twice with dimethylformamide. The residue was dissolved in dimethylformamide (10 mL). p-Toluenesulfonic acid monohydrate (catalytic) and 2,2-dimethoxypropane (4.6 mL, 32 mmol) were added. After stirring 4 hours at room temperature, the reaction mixture was diluted with ether and washed with saturated aqueous sodium bicarbonate and saturated aqueous sodium chloride. The organic layer was dried over sodium sulfate and concentrated under reduced pressure. The residue was purified by flash chromatography on silica gel (pentane/ether 70/30 to 40/60). Yield: 1.2 g, 50%, Rf=0.4 (silica gel, hexanes/ethyl acetate 60/40).

Example 16

Preparation of compound of formula 4

4-N-(4-fluorophenyl)amino-5-phenyl-7-(2,3-O-(methylethylidene)-4-spirocyclopropyl-β-D-erythro-furanosyl)pyrrolo[2,3-d]pyrimidine The title compound was synthesized following a procedure analogous to the synthesis described in example 12. Thus coupling of 2,3-O-(methylethylidene)-4-spirocyclopropyl-D-erythro-furanose (450 mg, 2.42 mmol) with 4-(4-fluorophenyl)amino-5-phenyl-pyrrolo[2,3-d]pyrimidine (20, 1.47 g, 4.84 mmol) provided the title nucleoside (294 mg, 26%), Rf=0.6 (silica gel, hexanes/ethyl acetate 70/30).

Example 17

Preparation of compound of formula 1

4-N-(4-fluorophenyl)amino-5-phenyl-7-(4-spirocyclopropyl-β-D-erythro-furanosyl)pyrrolo[2,3-d]pyrimidine; Table 4 #150

The title compound was synthesized following a procedure analogous to the synthesis described in Example 13. Thus 4-(4-fluorophenyl)amino-5-phenyl-7-(2,3-O-(methylethylidene)-4-spirocyclopropyl-β-D-erythro-furanosyl)pyrrolo[2,3-d]pyrimidine (289 mg, 0.6 mmol) provided the titled deprotected nucleoside (159 mg, 60%), Rf=0.5 (silica gel, dichloromethane/methanol 90/10), mp 142° C.

Example 18

Preparation of compound of formula 4

4-chloro-5-iodo-7-(5-deoxy-4-C-methyl-2,3-O-(methylethylidene)-β-D-ribofuranosyl)pyrrolo[2,3-d]pyrimidine The title compound was synthesized following a procedure analogous to the synthesis described in Example 12. Thus coupling of 5-deoxy-4-C-methyl-2,3-O-(methylethylidene)-D-ribofuranose (550 mg, 2.9 mmol) with 4-chloro-5-iodo-pyrrolo[2,3-d]pyrimidine (1.23 g, 4.35 mmol) provided the titled nucleoside (581 mg, 44%), Rf=0.4 (silica gel, hexanes/ethyl acetate 60/40).

Example 19

A. Preparation of compound of formula 1

4-chloro-5-iodo-7-(5-deoxy-4-C-methyl-β-D-ribofuranosyl)pyrrolo[2,3-d]pyrimidine The title compound was synthesized following a procedure analogous to the synthesis described in Example 13. Thus 4-chloro-5-iodo-7-(5-deoxy-4-C-methyl-2,3-O-(methylethylidene)-β-D-ribofuranosyl)pyrrolo-[2,3-d]pyrimidine (100 mg, 0.22 mmol) provided the titled deprotected nucleoside (14 mg, 15%), Rf=0.45 (silica gel, dichloromethane/methanol 90/10), mp 173°–174° C.

B. Preparation of compound of formula 4

4-chloro-5-iodo-7-(2,3-O-(methylethylidene)-4-spirocyclopropyl-β-D-erythro-furanosyl)pyrrolo[2,3-d]pyrimidine The title compound was synthesized following a procedure analogous to the synthesis described in Example 12. Thus coupling of 2,3-O-(methylethylidene)-4-spirocyclopropyl-D-erythro-furanose (500 mg, 2.66 mmol) with 4-chloro-5-iodo-pyrrolo[2,3-d]pyrimidine (1.11 g, 3.99 mmol) provided the titled nucleoside (402 mg, 34%), Rf=0.7 (silica gel, hexanes/ethyl acetate 70/30).

Example 20

Preparation of compound of formula 4

4-amino-5-iodo-7-(4-spirocyclopropyl-β-D-erythro-furanosyl)pyrrolo[2,3-d]pyrimidine; Table 4 #175

Liquid ammonia (15 mL) was added to a solution of 4-chloro-5-iodo-7-(2,3-O-(methylethylidene)-4-spirocyclopropyl-β-D-erythro-furanosyl)pyrrolo[2,3-d]pyrimidine (200 mg, 0.45 mmol) in methanol (15 mL) at −78° C. The reaction mixture was heated at 100° C. in a sealed steel bomb for 24 hours. Ammonia was slowly released from the cooled bomb and the resulting solution was concentrated under reduced pressure. The residue was disolved in 70% aqueous trifluoroacetic acid and stirred at room temperature. After 30 minutes the reaction mixture was concentrated under reduced pressure and azeotroped twice with water and twice with ethanol. The residue was neutralized with saturated aqueous sodium bicarbonate and the precipitated nucleoside was filtered and rinsed with water. The solid was recovered and recrystallized from ethanol. Yield: 73 mg, 42%, Rf=0.35 (silica gel, dichloromethane/methanol 90/10), mp 232° C. (dec).

Example 21

Preparation of compound of formula 12]

4-C-methyl-2,3,5-tri-O-(phenylmethyl)-1-(1,3-dithian-2-yl)-D-lyxo-pentane

The title compound was synthesized following a procedure analogous to the synthesis described in Example 9.

Thus the copound of Example 2 (5 g, 9.8 mmol) gave the title compound (3.94 g, 84%) from a separable 12/1 epimeric mixture, Rf=0.38 (silica gel, hexanes/ethyl acetate 70/30).

Example 22

Preparation of compound of formula 2

4-C-methyl-2,3,5-tri-O-(phenylmethyl)-D-lyxofuranose

The title compound was synthesized following a procedure analogous to the synthesis described in Example 4. Thus the compound of Example 2 (3.94 g, 7.51 mmol) gave the tile compound (2.6 g, 80%), Rf=0.25 (silica gel, hexanes/ethyl acetate 70/30).

Example 23

Preparation of compound of formula 4

4-N-[4-(N,N-dimethylaminomethyl)phenylamino]-5-phenyl-7-(4-C-methyl-2,3,5-tri-O-(phenylmethyl)-β-D-lyxofuranosyl)pyrrolo[2,3-d]pyrimidine The title compound was synthesized following a procedure analogous to the synthesis described in Example 12. Thus coupling of 4-C-methyl-2,3,5-tri-O-(phenylmethyl)-D-lyxofuranose (500 mg, 1.15 mmol) with 4-[4-(N,N-dimethylaminomethyl)phenylamino]-5-phenyl-pyrrolo[2,3-d]pyrimidine (593 mg, 1.5 mmol) provided an unseparable mixture of the title compound and its N1-isomer and Tris [2-(2-methoxyethoxy)ethyl]amine (836 mg); Rf=0.6 (silica gel, dichloromethane/methanol 90/10).

Example 24

Preparation of formula 1

4-[4-N-(N,N-dimethylaminomethyl)phenylamino]-5-phenyl-7-(4-C-methyl-β-D-lyxofuranosyl)pyrrolo[2,3-d]-pyrimidine An orange solution of palladium chloride (400 mg) in anhydrous methanol (10 mL) was degassed and stirred under hydrogen (1 atm) for 10 minutes. A solution of 4-[4-(N,N-dimethylaminomethyl)phenylamino]-5-phenyl-7-(4-C-methyl-2,3,5-tri-O-(phenylmethyl)-β-D-lyxofuranosyl)-pyrrolo[2,3-d]pyrimidine, its N1-isomer and Tris[2-(2-methoxyethoxy)ethyl]amine (786 mg) in solution in anhydrous methanol (10 mL) was added to the suspension of reduced palladium. The heterogeneous reaction mixture was stirred at room temperature under hydrogen (1 atm) for 6 hours, filtered through Celite® and the filtering pad was rinsed with boiling methanol. The combined filtrates were concentrated under reduced pressure. The residue was dissolved in 0.1N hydrochloric acid and washed twice with ethyl acetate. The pH of the aqueous solution was brought to 12 with 1N aqueous sodium hydroxide and the resulting solution was extracted 3 times with ethyl acetate. The combined organic extracts were dried over sodium sulfate and concentrated under reduced pressure. The residue was purified by flash chromatography on silica gel (dichloromethane/methanol/30% aqueous ammonium hydroxide 90/10/1 to 80/20/1). The partially purified nucleoside was further purified by HPLC (C18, 50×250 mm, methanol/(water/methanol/acetic acid 95/5/0.5) 45/55, 16.5 mL/minute, $\lambda_{max}$=299 nm, Rt=20.6 minutes) and crystallized from ethanol. Yield: 26.8 mg, Rf=0.25 (silica gel, dichloromethane/methanol 80/20), mp 205°–206° C.

Example 25

Preparation of compound of formula 12

4-C-methyl-2,3,5-tri-O-(phenylmethyl)-1-(1,3-dithian-2-yl)-d-ribo-pentane

A solution of the compound of Example 8 (4 g, 10 mmol) in dry tetrahydrofuran (100 mL) was added dropwise over 10 minutes to a solution of [(phenylmethyl)oxy] methyllithium (1.8 mmol) (Still, W. C. *J. Am. Chem. Soc.* 100, 1481 (1978)) in dry tetrahydrofuran (50 mL) at –78° C. After stirring for 10 minutes at –78° C., the reaction mixture was quenched by slow addition of a solution of acetic acid (2.3 mL) in dry tetrahydrofuran (50 mL) over 5 minutes at –78° C. The quenched solution was warmed to room temperature, diluted with ethyl acetate and washed with saturated aqueous ammonium chloride, saturated aqueous sodium bicarbonate and saturated aqueous sodium chloride. The organic layer was dried over sodium sulfate and concentrated under reduced pressure. The residue was purified by flash chromatography on silica gel (hexanes/ethyl acetate 90/10 to 75/25). Yield: 3.68 g, 70%, Rf=0.45 (silica gel, hexanes/ethyl acetate 70/30).

Example 26

Preparation of compound of formula 2

4-C-methyl-2,3,5-tri-O-(phenylmethyl)-D-ribofuranose

The title compound was synthesized following a procedure analogous to the synthesis described in Example 4. Thus the compound of Example 25 (3.68 g, 7 mmol) gave 2.22 g, 73%, Rf=0.25 (silica gel, hexanes/ethyl acetate 70/30).

Example 27

Preparation of compound of formula 4

4-N-phenylamino-5-phenyl-7-(4-C-methyl-2,3,5-tri-O-(phenylmethyl)-β-D-ribofuranosyl)pyrrolo[2,3-d]pyrimidine The title compound was synthesized following a procedure analogous to the synthesis described in Example 12. Thus coupling of 4-C-methyl-2,3,5-tri-O-(phenylmethyl)-D-ribofuranose (500 mg, 1.15 mmol) with 4-phenylamino-5-phenylpyrrolo[2,3-d]pyrimidine (494 mg, 1.73 mmol) provided the titled nucleoside (165 mg, 20%); Rf=0.6 (silica gel, hexanes/ethyl acetate 70/30).

Example 28

Preparation of compound of formula 1

4-N-phenylamino-5-phenyl-7-(4-C-methyl-β-D-ribofuranosyl)pyrrolo[2,3-d]pyrimidine The title compound was synthesized following a procedure analogous to the synthesis described in Example 24. Thus 4-phenylamino-5-phenyl-7-(4-C-methyl-2,3,5-tri-O-(phenylmethyl)-β-D-ribofuranosyl)pyrrolo-[2,3-d] pyrimidine (144 mg) provided the titled deprotected nucleoside (63 mg, 73%), Rf=0.45 (silica gel, dichloromethane/methanol 90/10), mp 211°–213° C.

Example 29

Preparation of compound of formula 4

4-N-[4-(N,N-dimethylaminomethyl)phenylamino]-5-phenyl-7-(2,3-O-(methylethylidene)-4-spirocyclopropyl-β-D-erythro-furanosyl)pyrrolo[2,3-d]pyrimidine The title compound was synthesized following a procedure analogous to the synthesis described in Example 12.

Thus coupling of 2,3-O-(methylethylidene)-4-spirocyclopropyl-D-erythro-furanose (350 mg, 1.88 mmol) with 4-[4-(N,N-dimethylaminomethyl)phenylamino]-5-phenyl-pyrrolo[2,3-d]pyrimidine (1.11 g, 3.99 mmol) provided an unseparable mixture of the titled nucleoside, its N1-isomer and Tris[2-(2-methoxyethoxy)ethyl]amine (1.31 g); Rf=0.45 (silica gel, dichloromethane/methanol 90/10).

Example 30

Preparation of compound of formula 1

4-N-[4-(N,N-dimethylaminomethyl)phenylamino]-5-phenyl-7-(4-spirocyclopropyl-β-D-erythro-furanosyl)pyrrolo-[2,3-d]pyrimidine; Table 4 #158

A mixture of 4-N-[4-(N,N-dimethylaminomethyl)phenylamino]-5-phenyl-7(2,3-O-(methylethylidene)-4-spirocyclopropyl-β-D-erythro-furanosyl)pyrrolo[2,3-d]pyrimidine, its N1-isomer and Tris[2-(2-methoxyethoxy)ethyl]amine (1.31 g) was dissolved in methanol (10 mL) and 0.1N hydrochloric acid (10 mL). The pH was adjusted to pH=1.5 with 6N hydrochloric acid (0.5 mL) and the homogeneous solution was refluxed for one hour. The reaction mixture was diluted with 0.1N hydrochloric acid and washed twice with ethyl acetate. The pH of the aqueous solution was brought to 12 with 1N aqueous sodium hydroxide and the resulting solution was extracted 3 times with ethyl acetate. The combined organic extracts were dried over sodium sulfate and concentrated under reduced pressure. The residue was purified by flash chromatography on silica gel (dichloromethane/methanol/30% aqueous ammonium hydroxide 90/10/1 to 80/20/1). The partially purified nucleoside was further purified by HPLC (C18, 50×250 mm, methanol/(water/methanol/acetic acid 95/5/0.5) 45/55, 18 mL/minute, $\lambda_{max}$=299 nm, Rt=17 minutes) and crystallized from ethyl acetate to provide the title compound (Rf=0.25 (silica gel, dichloromethane/methanol 80/20).

Example 31

Preparation of compound of formula 4

4-N-phenylamino-5-phenyl-7-(2,3-O-(methylethylidene)-β-D-erythrofuranosyl)pyrrolo[2,3-d]pyrimidine Oxalyl chloride (0.55 mL, 6.3 mmol) was added dropwise, keeping the temperature below 35° C., to a solution of N,N-dimethylformamide (4.8 mL, 63 mmol) in toluene (5.4 mL) and acetonitrile (1.9 mL). The slushy mixture was stirred at room temperature for 15 minutes then cooled to −12° C. A solution of 2,3-O-(methylethylidene)-β-D-erythrofuranose (1 g, 6.24 mmol) in toluene (1.2 mL) was added to the reaction mixture maintaing the temperature below −12° C., After stirring at −12° C. for 20 minutes the solution was cooled to −16° C. and a solution of triethylamine (1.1 mL, 7.9 mmol) in toluene (1 mL) was added maintening the temperature below 0° C. The precipitate was stirred 15 minutes at 0° C., filtered off over a pad of Celite® and rinsed with toluene. The combined filtrates were added to a mixture of 4-phenylamino-5-phenyl-pyrrolo[2,3-d]pyrimidine (2.85 g, 1 mmol), finely powdered potassium hydroxide (85%, 1.31 g, 2 mmol) and tris[2-(2-methoxyethoxy)ethyl]amine (4 mL, 1.25 mmol) in dry toluene which had been stirring at room temperature for 2 hours. After stirring overnight at room temperature, the reaction mixture was diluted with ethyl acetate and washed with saturated aqueous ammonium chloride. The organic layer was dried over sodium sulfate and concentrated under reduced pressure. The residue was purified by flash chromatography on silica gel (hexanes/ethyl acetate 70/30 to 50/50). Yield: 969 mg, 36%, Rf=0.55 (silica gel, hexanes/ethyl acetate 60/40).

Example 32

Preparation of compound of formula 1

4-N-phenylamino-5-phenyl-7-β-D-erythrofuranosyl) pyrrolo[2,3-d]pyrimidine; Table 1 #27

The title compound was synthesized following a procedure analogous to the synthesis described in Example 13. Thus 4-phenylamino-5-phenyl-7-(2,3-O-(methylethylidene) -β-D-erythrofuranosyl)pyrrolo[2,3-d]pyrimidine (40, 969 mg, 2.26 mmol) provided deprotected nucleoside 41 (401 mg, 46%), Rf=0.5 (silica gel, dichloromethane/methanol 90/10), mp 210.5°–211.5° C.

Example 33

Preparation of compound of formula 12

4-C-[(methoxy)methyl]-2,3,5-tri-O-(phenylmethyl)-1,3-dithian-2-yl)-D-lyxo-pentane A solution of the compound of Example 2 (1.02 g, 2 mmol) in dry tetrahydrofuran (40 mL) was added dropwise over 5 minutes to a solution of [(methyl)oxy]methyllithium (6 mmol) (Still, W. C. *J. Am. Chem. Soc.* 1978, 100, 1481) in dry tetrahydrofuran (40 mL) at −78° C. After stirring for 20 minutes at −78° C., the reaction mixture was quenched with saturated aqueous ammonium chloride, warmed to room temperature, diluted with ethyl acetate and washed with saturated aqueous ammonium chloride. The organic layer was dried over sodium sulfate and concentrated under reduced pressure. The residue was purified by flash chromatography on silica gel (hexanes/ethyl acetate 90/10 to 75/25). Yield: 0.48 g, 43%, Rf=0.45 (silica gel, hexanes/ethyl acetate 70/30).

Example 34

Preparation of compound of formula 2

4-C-methoxymethyl-2,3,5-tri-O-(phenylmethyl)-D-lyxofuranose

The title compound was synthesized following a procedure analogous to the synthesis described in Example 4. Thus the compound of Example 33 (3.53 g, 6.3 mmol) gave the title compound (1 g, 34%), Rf=0.25 (silica gel, hexanes/ethyl acetate 70/30).

Example 35

Preparation of compound of formula 4

4-N-(4-fluorophenyl)amino-5-phenyl-7-(4-C-methoxymethyl-2,3,5-tri-O-(phenylmethyl)-β-D-lyxofuranosyl)pyrrolo[2,3-d]pyrimidine The title compound was synthesized following a procedure analogous to the synthesis described in Example 12. Thus coupling of 4-C-methoxymethyl-2,3,5-tri-O-(phenylmethyl)-D-lyxofuranose (500 mg, 1.08 mmol) with 4-(4-fluorophenyl)amino-5-phenyl-pyrrolo[2,3-d] pyrimidine (0.5 g, 1.64 mmol) provided the title compound (328 mg, 40%); Rf=0.6 (silica gel, hexanes/ethyl acetate 70/30).

Example 36

Preparation of compound of formula 1

4-N-(4-fluorophenyl)amino-5-phenyl-7-(4-C-methoxymethyl-β-D-lyxofuranosyl)pyrrolo[2,3-d]pyrimidine The title compound was synthesized following a procedure analogous to the synthesis described in Example 24. Thus 4-(fluorophenyl)amino-5-phenyl-7-(4-C-methoxymethyl-2,3,5-tri-O-(phenylmethyl)-β-D-lyxofuranosyy)pyrrolo-[2,3-d]pyrimidine (430 mg) provided the titled deprotected nucleoside Rf=0.45 (silica gel, dichloromethane/methanol 90/10). MS, expected 481, found 481.

Example 37

Preparation of Compound of formula 4

1-(1,2,3-tri-O-acetyl-β-D-erythrofuranosyl)-3-(4-chlorophenyl)-4-N-phenylaminopyrazolo[3,4-d]pyrimidine A mixture of 1,2,3-tri-O-acetyl-D-erythrofuranose (619 mg, 2.5 mmol) obtained according to Kline, *J. Org. Chem.* 57:6, 1772 (1992), 3-(4-chlorophenyl)-4-phenylaminopyrazolo[3,4-d]pyrimidine (809 mg, 2.51 mmol.) obtained for example according to the methods in U.S. application Ser. No. 08/014,190, and boron trifluoride diethyl etherate (620 µL, 5 mmol) in nitromethane (20 mL) was refluxed for 1 hour. After cooling to room temperature, the reaction mixture was concentrated under reduced pressure. The residue was dissolved in ethyl acetate and poured into a stirring solution of saturated aqueous sodium bicarbonate. The layers were separated and the acqueous layer was extracted with ethyl acetate. The combined organic extracts were washed with saturated acqueous sodium chloride, dried over sodium sulfate and concentrated under reduced pressure. The residue was purified by flash chromatography on silica gel to provide the protected nucleoside.

Example 38

Preparation of compound of formula 1

1-(β-D-erythrofuranosyl)-3-(4-chlorophenyl)-4-N-phenylaminopyrazolo[3,4-d]pyrimidine 1-(1,2,3-tri-O-acetyl-β-D-erythrofuranosyl)-3-(4-chlorophenyl)-4-phenyl aminopyrazolo[3,4-d]pyrimidine (100 mg, 0.2 mmol) was dissolved in methanolic ammonia (5 mL) freshly prepared by bubbling anhydrous ammonia through 10 mL of anhydrous methanol at 0 C. for 10 minutes. After stirring at room temperature for 24 hours, the reaction mixture was concentrated under reduced pressure and the residue was purified by flash chromatography on silica gel. Crystalization from ethanol gives the deprotected erythropyrazolopyrimidine. MS, expected MH⁺ 424, found 424. Rf=0.6, (silica, 90:10, $CH_2Cl_2$-Methanol)/

Example 39

Preparation of the Representative Heterocycles

Heterocycles, as shown in Scheme 14, are made in the following manner.

A. Preparation of compound of formula 37 (2-Amino-3-cyano-4-phenylpyrrole)

To a solution of phenacyl chloride (500 g, 3.23M) in dry N,N-dimethylformamide (600 mL) was added potassium phthalimide, (600 g, 3.23M) in small portions. The resulting mixture was stirred at ambient temperature overnight. To this was added malononitrile (256 g, 3.88M) in one lot followed by a 25 wt % solution of sodium methoxide in methanol (744 mL, 3.2 mol). The resulting mixture was stirred at room temperature overnight. Ice-water (10.0 L) was added to the reaction mixture and stirring was continued at room temperature overnight. The precipitate formed was collected by filtration and washed with cold water (4.0 L). The off-white solid was stirred in toluene (3.0 L) and filtered. The solid was washed with toluene (300 mL) and dried under vacuum at 60 C. overnight. Yield 298.56 g. m.p. 172–174 C.

B. Preparation of compound of formula 39 (5-Phenyl-4-N-(4-fluorophenyl)aminopyrrolo[2,3-d]pyrimidine)

A mixture of the compound of Example 39A (296.0 g, 1.62 mol) and triethylorthoformate (3.2 L) was refluxed for 1 h. The triethylorthoformate was distilled off under reduced pressure until the pot temperature reached 88 C. To the cooled reaction mixture hexane(3.0 L) was added with vigorous stirring. The contents of the vessel were cooled to 0 C. and the off-white solid formed was collected by filtration and washed with hexane (2×500 mL) and dried under suction. Final drying was done in a high vacuum oven. Yield of the 2-ethoxymethylene-3-cyano-4-phenylpyrrole was 323.0 g (83%). m.p. 98–100 C.

The above material (100 g, 0.42 mol) was dissolved in 1,2-dichlorobenzene. 4-Fluoroaniline (60 mL, 0.62 mol) was added and the reaction mixture was heated to 125 C. for 1 h. An additional 985 mL of 1,2-dichlorobenzene was added and the reaction temperature was raised to 140 C. for 3 h. Upon cooling to 0 C. the title compound precipitated as a yellow solid which was collected by filtration and dried under vacuum. Yield 66.0 g. m.p. 215–218 C.

C. Preparation of compound of formula 39

4-N-(4-N,N-Dimethylaminomethylphenyl)amino-5-phenyl-pyrrolo[2,3-d]Pyrimidine

This compound was made by a route similar to Example 39B. Here, the fluoroaniline was replaced with 4-N,N-dimethylaminomethylaniline. m.p. 208–209 C.

D. Preparation of compound of formula 39

5-Phenyl-4-phenylaminopyrrolo[2,3-d]pyrimidine

This compound was made by a route similar to Example 39B. Here, the fluoroaniline was replaced by aniline. m.p. 208–209 C.

Example 40

Representative C-4'-Symetrically Substituted Pyrrolo Pyrimidine Nucleosides

Representative compounds of the invention, which can be made according to the methods described above, are identified in the following tables. With reference to Formula 1, preferred compounds of the invention are pyrrolo pyrimidines (Y is carbon) where the A and B substituents are the same.

In one group of preferred compounds A and B are both $HOCH_2$; in another, A and B are both hydrogen. G is preferably hydrogen, and E is preferably hydrogen or bromine, most preferably hydrogen. $Z_1$ and $Z_2$ are preferably hydrogen or methyl, most preferably hydrogen.

TABLE 1

C4'-SYMETRICALLY SUBSTITUTED PYRROLO PYRIMIDINE NUCLEOSIDES
Y = C   E = G = $Z_1$ = $Z_2$ = H

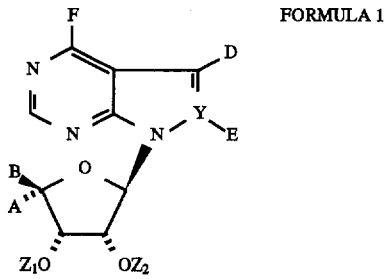

FORMULA 1

| A = B = HOCH$_2$ | A = B = H | F | D |
|---|---|---|---|
| 1 | 27 | phenylamino | phenyl |
| 2 | 28 | 4-fluorophenylamino | phenyl |
| 3 | 29 | 4-fluorophenylamino | 4-fluorophenyl |
| 4 | 30 | 4-fluorophenylamino | 4-hydroxyphenyl |
| 5 | 31 | 4-hydroxyphenylamino | phenyl |
| 6 | 32 | 4-hydroxymethylphenylamino | phenyl |
| 7 | 33 | 4-fluorophenylamino | 3-pyridyl |
| 8 | 34 | 3-pyridylamino | phenyl |
| 9 | 35 | phenylmethylamino | phenyl |
| 10 | 36 | 4-(N,N-dimethylaminomethyl)phenylamino | phenyl |
| 11 | 37 | 4-(N,N-diethylethylenediaminoethyl)-phenylamino | phenyl |
| 12 | 38 | 4-fluorophenylamino | 4-(N,N-dimethylaminoethyl)phenyl |
| 13 | 39 | 4-cyanophenylamino | phenyl |
| 14 | 40 | 4-fluorophenylamino | 4-cyanophenyl |
| 15 | 41 | 4-(2-N,N-dimethylaminoethyl carbamoyl)phenylamino | phenyl |
| 16 | 42 | 4-(1-morpholinomethyl)phenyl amino | phenyl |
| 17 | 43 | 4-(1-piperazinoethyl)phenylamino | phenyl |
| 18 | 44 | 4-fluorophenylamino | 4-(1-piperazinomethyl)phenyl |
| 19 | 45 | 4-(sulfonamido)phenylamino | phenyl |
| 20 | 46 | 4-(N-trifluoromethanesulfonyl amino)-phenylamino | phenyl |
| 21 | 47 | 4-fluorophenylamino | 4-(N-trifluoromethanesulfonylamino) phenyl |
| 22 | 48 | 4-guanidinophenylamino | phenyl |
| 23 | 49 | 4-fluorophenylamino | 4-guanidinophenyl |
| 24 | 50 | 4-(guanidinomethyl)phenylamino | phenyl |
| 25 | 51 | 4-amidinophenylamino | phenyl |
| 26 | 52 | 4-fluorophenylamino | 4-amidinophenyl |

When E is bromine and A and B are both HOCH$_2$ a preferred compound is one where (53) F is 4-fluorophenylamino and D is phenyl. Using the same definitions for D, E, F, G, and $Z_1$, $Z_2$, another preferred compound is one where (54) A and B are both hydrogen.

Example 41

Representative C-4' Unsymetrically Substituted Pyrrolo Pyrimidine Nucleosides Other preferred pyrolo pyrimidine compounds of the invention are those where A and B are not the same, as shown in Tables 2 and 3.

TABLE 2

C-4'-UNSYMETRICALLY SUBSTITUTED PYRROLO PYRIMIDINE NUCLEOSIDES
Y = C   E = G = $Z_1$ = $Z_2$ = H

| A = HOCH$_2$ B = CH$_3$ | B = HOCH$_2$ A = CH$_3$ | F | D |
|---|---|---|---|
| 55 | 81 | phenylamino | phenyl |
| 56 | 82 | 4-fluorophenylamino | phenyl |
| 57 | 83 | 4-fluorophenylamino | 4-fluorophenyl |
| 58 | 84 | 4-fluorophenylamino | 4-hydroxyphenyl |
| 59 | 85 | 4-hydroxyphenylamino | phenyl |

TABLE 2-continued

C-4'-UNSYMETRICALLY SUBSTITUTED PYRROLO PYRIMIDINE NUCLEOSIDES
Y = C  E = G = $Z_1$ = $Z_2$ = H

| A = $HOCH_2$<br>B = $CH_3$ | B = $HOCH_2$<br>A = $CH_3$ | F | D |
|---|---|---|---|
| 60 | 86 | 4-hydroxymethylphenylamino | 4-fluorophenyl |
| 61 | 87 | 4-fluorophenylamino | 3-pyridyl |
| 62 | 88 | 3-pyridylamino | phenyl |
| 63 | 89 | phenylmethylamino | phenyl |
| 64 | 90 | 4-(N,N-dimethylaminomethyl)phenylamino | phenyl |
| 65 | 91 | 4-(N,N-diethylethylenediaminoethyl)-phenylamino | phenyl |
| 66 | 92 | 4-fluorophenylamino | 4-(N,N-dimethylaminoethyl)phenyl |
| 67 | 93 | 4-cyanophenylamino | phenyl |
| 68 | 94 | 4-fluorophenylamino | 4-cyanophenyl |
| 69 | 95 | 4-(2-N,N-dimethylaminoethyl carbamoyl)-phenylamino | phenyl |
| 70 | 96 | 4-(1-morpholinomethyl)phenylamino | phenyl |
| 71 | 97 | 4-(1-piperazinoethyl)phenylamino | phenyl |
| 72 | 98 | 4-fluorophenylamino | 4-(1-piperazinomethyl)phenyl |
| 73 | 99 | 4-(sulfonamido)phenylamino | phenyl |
| 74 | 100 | 4-(N-trifluoromethanesulfonyl amino)-phenylamino | phenyl |
| 75 | 101 | 4-fluorophenylamino | 4-(N-trifluoromethane-sulfonyl amino)phenyl |
| 76 | 102 | 4-guanidinophenylamino | phenyl |
| 77 | 103 | 4-fluorophenylamino | 4-guanidinophenyl |
| 78 | 104 | 4-(guanidinomethyl)phenylamino | phenyl |
| 79 | 105 | 4-amidinophenylamino | phenyl |
| 80 | 106 | 4-fluorophenylamino | 4-amidinophenyl |

When E is bromine, A is $HOCH_2$ and B is $CH_3$, a preferred compound is one where (107) F is 4-fluorophenylamino and D is phenyl. Using the same definitions for D, E, F, G, and $Z_1$, $Z_2$, another preferred compound is one where (108) A is $CH_3$ and B is $HOCH_2$.

Example 42

Additional C-4' Unsymetrically Substituted Pyrrolo Pyrimidine Nuclesides

Still other prefered pyrolo pyrimidine compounds of the invention are those where one of A and B is $CH_3$ and the other is $H_2NCH_2$, as shown in Table 3.

TABLE 3

MORE C-4'-UNSYMETRICALLY SUBSTITUTED PYRROLO PYRIMIDINE NUCLEOSIDES
Y = C  E = G = $Z_1$ = $Z_2$ = H

| A = $HOCH_2$<br>B = $CH_3$ | A = $HOCH_2$<br>B = $CH_3$ | F | D |
|---|---|---|---|
| 109 | 128 | phenylamino | phenyl |
| 110 | 129 | 4-fluo(ophenylamino | phenyl |
| 111 | 130 | 4-fluorophenylamino | 4-fluorophenyl |
| 112 | 131 | 4-fluorophenylamino | 4-hydroxyphenyl |
| 113 | 132 | 4-hydroxyphenylamino | phenyl |
| 114 | 133 | 4-hydroxymethylphenylamino | phenyl |
| 115 | 134 | phenylamino | 3-pyridyl |
| 116 | 135 | 3-pyridylamino | phenyl |
| 117 | 136 | phenylmethylamino | phenyl |
| 118 | 137 | 4-cyanophenylamino | phenyl |
| 119 | 138 | 4-fluorophenylamino | 4-cyanophenyl |
| 120 | 139 | 4-carbamoylphenylamino | phenyl |
| 121 | 140 | 4-(sulfoamido)phenylamino | phenyl |
| 122 | 141 | 4-(N-trifluoromethanesulfonyl amino)phenylamino | phenyl |
| 123 | 142 | phenylamino | 4-(N-trifluoromethanesulfonylamino)phenyl |
| 124 | 143 | 4-guanidinophenylamino | phenyl |
| 125 | 144 | 4-fluorophenylamino | 4-guanidinophenyl |
| 126 | 145 | 4-amidinophenylamino | phenyl |
| 127 | 146 | 4-fluorophenylamino | 4-amidinophenyl |

When E is bromine, A is $NH_2CH_2$ and B is $CH_3$, a preferred compound is one where (147) F is 4-fluorophenylamino and D is phenyl. Using the same definitions for D, E, F, G, and $Z_1$, $Z_2$, another preferred compound is one where (148) A is $CH_3$ and B is $NH_2CH_2$.

Example 43

Representative C-4' Spirocyclic Pyrrolo Pyrimidine Nucleosides

A and B can together form a cyclopropyl ring. Prefered pyrolo compounds of this kind, where E, G, $Z_1$ and $Z_2$ are all hydrogen, are shown in Table 4.

TABLE 4

C-4' SPIROCYCLIC PYRROLO PYRIMIDINE NUCLEOSIDES
A & B FORM A RING   Y = C   E = G = $Z_1$ = $Z_2$ = H

| | F | D |
|---|---|---|
| 149 | phenylamino | phenyl |
| 150 | 4-fluorophenylamino | phenyl |
| 151 | 4-fluorophenylamino | 4-fluorophenyl |
| 152 | 4-fluorophenylamino | 4-hydroxyphenyl |
| 153 | 4-hydroxyphenylamino | phenyl |
| 154 | 4-hydroxymethylphenylamino | 4-fluorophenyl |
| 155 | 4-fluorophenylamino | 3-pyridyl |
| 156 | 3-pyridylamino | phenyl |
| 157 | phenylmethylamino | phenyl |
| 158 | 4-(N,N-dimethylaminomethyl)phenylamino | phenyl |
| 159 | 4-(N,N-diethylethylenediaminoethyl)phenylamino | phenyl |
| 160 | 4-fluorophenylamino | 4-(N,N-dimethylaminoethyl)phenyl |
| 161 | 4-cyanophenylamino | phenyl |
| 162 | 4-fluorophenylamino | 4-cyanophenyl |
| 163 | 4-(2-N,N-dimethylaminoethylcarbamoyl)phenylamino | phenyl |
| 164 | 4-(1-morpholinomethyl)phenylamino | phenyl |
| 165 | 4-(1-piperazinoethyl)phenylamino | phenyl |
| 166 | 4-fluorophenylamino | 4-(1-piperazinomethyl)phenyl |
| 167 | 4-(sulfonamido)phenylamino | phenyl |
| 168 | 4-(N-trifluoromethanesulfonylamino)phenylamino | phenyl |
| 169 | 4-fluorophenylamino | 4-(N-trfluoromethanesulfonylamino)phenyl |
| 170 | 4-guanidinophenylamino | phenyl |
| 171 | 4-fluorophenylamino | 4-guanidinophenyl |
| 172 | 4-(guanidinomethyl)phenylamino | phenyl |
| 173 | 4-amidinophenylamino | phenyl |
| 174 | 4-fluorophenylamino | 4-amidinophenyl |
| 175 | amino | iodo |

When E is bromine, and A and B form a cyclopropyl ring, a preferred compound is one where (176) F is 4-fluorophenylamino and D is phenyl.

Example 44

Representative C-4' Symetrically Substituted Pyrazo Pyrimidine Nucleosides

An additional group of prefered compound are the pyrazo pyrimidines, where Y is nitrogen and E is nothing. Representative gem pyrazo compounds, where A and B are the same (in this case both hydrogen) are shown in Table 5.

TABLE 5

C-4' SYMMETRICALLY SUBSTITUTED PYRAZO PYRIMIDINE NUCLEOSIDES
Y = N   G = $Z_1$ = $Z_2$ = H

| A = B = H | F | D |
|---|---|---|
| 177 | phenylamino | phenyl |
| 178 | 4-fluorophenylamino | phenyl |
| 179 | 4-fluorophenylamino | 4-fluorophenyl |
| 180 | 4-fluorophenylamino | 4-hydroxyphenyl |
| 181 | 4-hydroxyphenylamino | phenyl |
| 182 | 4-hydroxymethylphenylamino | 4-fluorophenyl |
| 183 | 4-fluorophenylamino | 3-pyridyl |
| 184 | 3-pyridylamino | phenyl |
| 185 | phenylmethylamino | phenyl |
| 186 | 4-(N,N-dimethylaminomethyl)phenylamino | phenyl |
| 187 | 4-(N,N-diethylethylenediaminoethyl)phenylamino | phenyl |
| 188 | 4-fluorophenylamino | 4-(N,N-dimethylaminoethyl)phenyl |
| 189 | 4-cyanophenylamino | phenyl |
| 190 | 4-fluorophenylamino | 4-cyanophenyl |
| 191 | 4-(2-N,N-dimethylaminoethylcarbamoyl)-phenylamino | phenyl |
| 192 | 4-(1-morpholinomethyl)phenylamino | phenyl |
| 193 | 4-(1-piperazinoethyl)phenylamino | phenyl |
| 194 | 4-fluorophenylamino | 4-(1-piperazinomethyl)phenyl |
| 195 | 4-(sulfonamido)phenylamino | phenyl |
| 196 | 4-(N-trifluoromethanesulfonylamino)phenylamino | phenyl |
| 197 | 4-fluorophenylamino | 4-(N-trfluoromethanesulfonylamino)phenyl |
| 198 | 4-guanidinophenylamino | phenyl |
| 199 | 4-fluorophenylamino | 4-guanidinophenyl |
| 200 | 4-(guanidinomethyl)phenylamino | phenyl |
| 201 | 4-amidinophenylamino | phenyl |
| 202 | 4-fluorophenylamino | 4-amidinophenyl |

Example 45

C-4' Unsymetrically Substituted Pyrazolo Pyrimidine Nucleosides

Still other prefered pyrazolo pyrimidine compounds of the invention are those where one of A and B is $CH_3$ and the other is $H_2NCH_2$, as shown in Table 6.

TABLE 6

MORE C-4' UNSYMETRICALLY SUBSTITUTED PYRAZOLO PYRIMIDINE NUCLEOSIDES
Y = C   E = G = $Z_1$ = $Z_2$ = H

| A = $CH_3$ B = $H_2NCH_2$ | A = $H_2NCH_2$ B = $CH_3$ | F | D |
|---|---|---|---|
| 203 | 222 | phenylamino | phenyl |
| 204 | 223 | 4-fluorophenylamino | phenyl |
| 205 | 224 | 4-fluorophenylamino | 4-fluorophenyl |
| 206 | 225 | 4-fluorophenylamino | 4-hydroxyphenyl |
| 207 | 226 | 4-hydroxyphenylamino | phenyl |
| 208 | 227 | 4-hydroxymethylphenylamino | phenyl |

TABLE 6-continued

MORE C-4' UNSYMETRICALLY SUBSTITUTED PYRAZOLO PYRIMIDINE NUCLEOSIDES
Y = C  E = G = $Z_1$ = $Z_2$ = H

| A = $CH_3$<br>B = $H_2NCH_2$ | A = $H_2NCH_2$<br>B = $CH_3$ | F | D |
|---|---|---|---|
| 209 | 228 | 4-fluorophenylamino | 3-pyridyl |
| 210 | 229 | 3-pyridylamino | phenyl |
| 211 | 230 | phenylmethylamino | phenyl |
| 212 | 231 | 4-cyanophenylamino | phenyl |
| 213 | 232 | 4-carbamoylphenylamino | phenyl |
| 214 | 233 | 4-fluorophenylamino | 4-cyanophenyl |
| 215 | 234 | 4-(sulfonamido)phenylamino | phenyl |
| 216 | 235 | 4-(N-trifluoromethanesulfony amino)-phenylamino | phenyl |
| 217 | 236 | 4-fluorphenylamino | 4-(N-trifluoromethanesulfonylamino) phenyl |
| 218 | 237 | 4-guanidinophenylamino | phenyl |
| 219 | 238 | 4-fluorophenylamino | 4-guanidinophenyl |
| 220 | 239 | 4-amidinophenylamino | phenyl |
| 221 | 240 | 4-fluorophenylamino | 4-amidinophenylamino |

Example 46

Representative C-4' Spirocyclic Pyrazolo Pyrimidine Nucleosides

A and B can together form a cyclopropyl ring. Preferred pyrazolo pyrimidine nucleosides of this kind, where G, $Z_1$ and $Z_2$ are all hydrogen, are shown in Table 7.

TABLE 7

C-4' SPIROCYCLIC PYRAZOLO PYRIMIDINE NUCLEOSIDES
A & B FORM A RING  Y = N  G = $Z_1$ = $Z_2$ = H

| F | D |
|---|---|
| 241 phenylamino | phenyl |
| 242 4-fluorophenylamino | phenyl |
| 243 phenylamino | 4-chlorophenyl |
| 244 4-fluorophenylamino | 4-hydroxyphenyl |
| 245 4-hydroxyphenylamino | phenyl |
| 246 4-methoxyphenylamino | phenyl |
| 247 4-hydroxymethylphenylamino | phenyl |
| 248 4-fluorophenylamino | 3-pyridyl |
| 249 3-pyridylamino | phenyl |
| 250 phenylmethylamino | phenyl |
| 251 4-(N,N-dimethylaminomethyl)phenyl-amino | phenyl |
| 252 4-(N,N-diethylethylenediaminoethyl) phenylamino | phenyl |
| 253 4-fluorophenylamino | 4-(N,N-dimethylamino-ethyl)phenyl |
| 254 4-cyanophenylamino | phenyl |
| 255 4-fluorophenylamino | 4-cyanophenyl |
| 256 4-(2-N,N-dimethylaminoethyl-carbamoyl)phenylamino | phenyl |
| 257 4-(1-morpholinomethyl)phenylamino | phenyl |
| 258 4-(1-piperazinoethyl)phenylamino | phenyl |
| 259 4-fluorophenylamino | 4-(1-piperazino-methyl)phenyl |
| 260 4-(sulfonamido)phenylamino | phenyl |
| 261 4-(N-trifluoromethanesulfonylamino) phenylamino | phenyl |
| 262 4-fluorophenylamino | 4-(N-trifluoromethane-sulfonylamino)phenyl |
| 263 4-guanidinophenylamino | phenyl |
| 264 4-fluorophenylamino | 4-guanidinophenyl |
| 265 4-(guanidinomethyl)phenylamino | phenyl |
| 266 4-amidiniphenylamino | phenyl |

UTILITY

The adenosine kinase inhibitors of the present invention may be used in the treatment of a variety of clinical situations where increasing local levels of adenosine are beneficial. The compounds of the invention act as potent inhibitors of adenosine kinase in vitro, and the present compounds in particular are orally available.

Adenosine has been proposed to serve as a natural anti-convulsant. Compounds of the present invention which enhance adenosine levels are useful in seizure disorders, as shown in animal models of seizures detailed below. Adenosine kinase inhibitors may be used in the treatment of patients with seizures or epilepsy or patients who might have chronic low or insufficient adenosine levels or might benefit from increased adenosine such as those suffering from autism, cerebral palsy, insomnia or other neuropsychiatric symptoms.

Adenosine kinase inhibitors of the invention find further utility in the treatment of acute pain, including but not limited to peri-operative, post-surgical, and end-stage cancer pain. Compounds of the invention are also useful in controlling chronic pain, including but not limited to pain caused by arthritis, cancer, trigeminal neuralgia, multiple sclerosis, neuropathies such as those arising from diabetes and AIDS and in addition, lower back pain and phantom limb pain. Treatment of acute and chronic pain can be treated by administration of the compounds of the invention in a systemic or oral fashion, as illustrated by animal models detailed below.

Adenosine has been reported to be an endogenous modulator of inflammation by virtue of its effects on stimulated neutrophil function and on macrophage, lymphocyte and platelet function. The compounds of this invention may therefore be used in treating conditions in which inflammatory processes are prevalent such as arthritis, reperfusion injury, and other inflammatory disorders.

The compounds of the invention are also useful in the treatment of chronic neurodegenerative disease, such as Alzheimer's disease, Parkinson's deisease, ALS, Huntington's disease, and AIDS dimentia.

Stroke and central nervous system ("CNS") trauma are conditions where tissue injury results from reduced blood supply to the CNS and are thus amenable to an intervention that provides increased levels of adenosine to the compromised tissue. It is reported that a significant component of the neurodegeneration resulting from stroke or CNS trauma is caused by increased excitatory amino acid release and sensitivity, which results in neurons being stimulated to death. In addition to vasodilatory properties, adenosine has been reported to inhibit release of excitatory amino acids (Burke and Nadler *J. Neurochem.*, 1988, 51:1541) and responsiveness of neurons to excitation. The compounds of this invention, which increase adenosine levels, may also be used in the treatment of conditions where release of or sensitivity to excitatory amino acids is implicated.

To assist in understanding the present inventions and especially their properties and utilities, the results of a series of experiments are also included. These experiments demonstrated that a number of compounds of the present invention were potent inhibitors of a purified cardiac adenosine kinase. Certain adenosine kinase inhibitors were found to inhibit seizures and exhibit anti-inflammatory activity in well-established animal models. The results of these experiments are shown in Table 8.

TABLE 8

UTILITY OF REPRESENTATIVE COMPOUNDS

| # | Name | ($IC_{50}$) AK Inhibition (nM) | Carrageenan Paw (% inh) p.o. | Carrageenan Paw (% inh) i.p. | Anticonvulsant Activity (MES) i.p. (mg/kg) |
|---|---|---|---|---|---|
| 1 | 4-phenylamino-5-phenyl-7-(4-hydroxy-methyl-1-β-D-ribofuranosyl)pyrrolo[2,3-d]pyrimidine (m.p. 232 C) | 1.2 | 18.10 | 2.80 | >1.00 |
| 150 | 4-N-(4-fluorophenyl-amino)-5-phenyl-7-(4-spirocyclopropyl-β-D-erythrofuranosyl)pyrrolo[2,3-d]pyrimidine (m.p. 142 C) | 0.3 | 80.30 | 78.00 | 0.23 |
| 175 | 4-amino-5-iodo-7-(4-spirocyclopropyl-β-D-erythrofuranosyl)pyrrolo[2,3-d]pyrimidine (m.p. 232 C) | 600.0 | | | |
| 81 | 4-(phenylamino)-5-phenyl-7-(4-C-methyl-B-D-ribfuranosyl)pyrrolo[2,3-d]pyrimidine (m.p. 211-213 C) | 2000.0 | | | |
| 64 | 4-[4-(N,N-dimethyl-aminomethyl)phenyl-amino]-5-phenyl-7-(4-C-methyl-B-D-lyxo-furanosyl)pyrrolo[2,3-d]pyrimidine (m.p. 205-206 C) | 70.0 | | | >5.0 |
| 27 | 4-phenylamino-5-phenyl-7-(1-β-D-erythrofuranosyl)-pyrrolo[2,3-d]pyrimidine (m.p. 210-211 C). | 4.0 | | | <5.0 |

AK INHIBITION

Adenosine kinase activity was measured essentially as described by Yamada et al. (Yamada, Y., Goto, H., Ogasawara, N. (1988) *Biochim. Biophys. Acta* 660, 36–43.) with a few minor modifications. Assay mixtures contained 50 mM TRIS-maleate buffer, pH 7.0, 0.1% BSA, 1 mM ATP 1 mM $MgCl_2$, 0.5 μM [U-$^{14}$C] adenosine (400–600 mCi/mmol) and varying duplicate concentrations of inhibitor. The reactions were initiated by addition of approximately 0.1 μU partially purified pig heart adenosine kinase, where one unit is defined as that amount of enzyme required to phosphorylate 1 μmol adenosine per minute. The reactions were incubated for 20 minutes at 37° C. The assay was quenched upon spotting 30 μL aliquots onto 2 $cm^2$ pieces of Whatman DE81 anion exchange paper. The paper squares were washed for 3 minutes in 6 L distilled/deionized water to remove the unreacted adenosine. The washed squares were rinsed in 95% ethanol and dried in an oven at 100° C. for 10 minutes. The amount of $^{14}$C-AMP was quantified by scintillation counting. The concentration of inhibitor required to inhibit 50% of the adenosine kinase activity ($IC_{50}$) was determined graphically. The results for representative adenosine kinase inhibitors of the invention are shown in Table 8.

ANTICONVULSANT ACTIVITY

The anticonvulsant activity of the tested compounds was evaluated in male SA rats (100–150 g, Simonsen) using the maximal electroshock (MES) model described in Swinyard et al., *Antiepileptic Drugs*, 3d Ed. at 85–102 (Levy, et al., eds.), New York: Raven Press (1989). The rats were maintained on a 12/12 light/dark cycle in temperature controlled facilities with free access to food and water. For p.o. administration, the animals are fasted overnight, prior to the experiment. One hour prior to seizure testing, the animals were injected interperitoneally (ip) or orally (per os, po) with one of various doses of test compound dissolved in DMSO or PEG 400.

Maximal electroshock seizures (MES) were induced by administering a 150 mA, 60 Hz current for 0.2 seconds via corneal electrodes using a Wahlquist Model H stimulator. The endpoint measurement was suppression of hind limb tonic extension (HTE), which was judged to occur when any hind leg extension did not exceed a 90 degree angle with the plane of the body. HTE suppression of this kind indicates that the test compound has the ability to inhibit seizures, in theory by inhibiting seizure propagation and spread, if not by raising the seizure threshold (i.e. preventing seizure potential). This endpoint was expressed as the percentage of animals in which the response was inhibited. Typically, compounds were screened initially at one hour following a dose of 5 mg/kg ip. In some cases, the effective dose at which 50% of the rats were protected ($ED_{50}$) was calculated from a dose response curve. The results for exemplary compounds of the invention are set forth in Table 8, expressed as $ED_{50}$ values. For compounds where the $ED_{50}$ was not calculated, the result is listed as >5 if HTE was inhibited in fewer than 50% of the animals in the intial screen, or <5 if HTE was inhibited in more than 50% of the animals in the intial screen.

ANTI-INFLAMMATORY ACTIVITY

Carrageenan (Type λ) was suspended in sterile PBS at 1% (w/v), autoclaved for 30 minutes, and stored at room temperature. Rats were pretreated with vehicle or AK inhibitor (10 mg/kg) by oral gavage or i.p. administration and the volume of the left hind paw was measured using a water displacement plethysmometer (Stoelting Co., Wood Dale, Ill.). One hour after oral treatment or 30 minutes after i.p. treatment, the rats were brieflt anesthatized, and 0.1 ml of the carrageenan solution was injected subcutaneously into the planar surface of the left hind paw. The ensuing paw swellin was measured by plethysmometry after 3 hours. The paw volume in millileters was subtracted from the pre-injection paw volume. Data are presented in Table 8 as the percent inhibition of paw swelling in AK inhibitor treated animals, compared to vehicle treated control animals. Rosengren et al., *J. Immunology* 154:5444–51 (1995).

FORMULATIONS

Compounds of the invention are administered to the affected tissue at the rate of from 0.1 to 200 nmole/min/kg, preferably from 1 to 50 nmol/min/kg. Such rates are easily maintained when soluble compounds are intravenously administered as discussed below. When other methods are used (e.g., oral administration), use of time-release preparations to control the rate of release of the active ingredient may be preferred. These compounds are administered in a dose of about 0.01 mg/kg/day to about 100 mg/kg/day, preferably from about 0.1 mg/kg/day to about 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 1000 μmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 0.1 to about 15 μmoles of the active ingredient per ML of solution so that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation and use can be understood further by the representative examples above, which illustrate the various aspects of the invention without limiting its scope.

We claim:

1. C-4'-modified phenyl pyrrolo[2,3-d] and pyrazolo[3,4-d]pyrimidine nucleoside analogs of the formula:

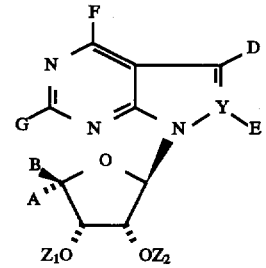

wherein:

A and B are both hydrogen;

A and B are each independently alkenyl, the group $(CH_2)_nQ$, where n is from 1 to 4 and Q is hydrogen, hydroxy, alkyl, alkoxy, amino, azido, or halogen;

or A and B together form a ring of from 3 to 6 carbons, the ring containing 0 to 3 heteroatoms selected from oxygen and nitrogen and optionally substituted by Q as defined above;

D is halogen, aryl, aralkyl, alkynyl, haloalkyl, cyano, carboxamido;

E is nothing when Y is nitrogen; and is hydrogen, halogen, or alkyl when Y is carbon;

F is alkyl, aryl, aralkyl, halogen, amino, alkylamino, arylamino, aralkylamino, alkoxy, aryloxy, aralkyloxy, alkylthio, arylthio, aralkylthio;

G is hydrogen or halogen;

Y is carbon or nitrogen;

$Z_1$ and $Z_2$ are independently hydrogen, acyl, or taken together form a cyclic carbonate;

and pharmaceutically acceptable salts thereof.

2. A compound of claim 1, where Y is carbon.

3. A compound of claim 1, where Y is nitrogen.

4. A compound of any one of claims 1–3 where A and B are the same.

5. A compound of any one of claims 1–3 where A and B are the same, but are not both methyl.

6. A compound of any one of claims 1–3 where A and B are both hydrogen.

7. A compound of any one of claims 1–3 where A and B are different.

8. A compound of any one of claims 1–3 where D is halogen, aryl, cyano, or CONRR', where R and R' are independently hydrogen or alkyl.

9. A compound of any one of claims 1–3 where F is amino, arylamino, halogen or alkyl.

10. A compound of claim 1, where G and each Z are hydrogen.

11. A compound of claim 2, where E, G, and each Z are hydrogen.

12. A compound of claim 3, where G and each Z are hydrogen.

13. A compound of any one of claims 10–12 where A and B are the same.

14. A compound of any one of claims 10–12 where A and B are the same, but are not both methyl.

15. A compound of any one of claims 10–12 where A and B are both hydrogen.

16. A compound of any one of claims 10–12 where A and B are different.

17. A compound of any one of claims 10–12 where D is aryl.

18. A compound of any one of claims 10–12 where F is arylamino.

19. A compound of any one of claims 1–3 where F is arylamino and D is aryl.

20. A compound of any one of claims 10–12 where F is arylamino and D is aryl.

21. A compound of claim 1, where A and B together form a ring of 3 to 6 carbons, the ring containing 0 to 3 heteroatoms selected from oxygen and nitrogen and optionally substituted by hydrogen, hydroxy, alkyl, alkoxy, amino, azido or halogen.

22. A compound of claim 2, where A and B together form a ring of 3 to 6 carbons, the ring containing 0 to 3 heteroatoms selected from oxygen and nitrogen and optionally substituted by hydrogen, hydroxy, alkyl, alkoxy, amino, azido or halogen.

23. A compound of claim 3, where A and B together form a ring of 3 to 6 carbons, a ring containing 0 to 3 heteroatoms selected from oxygen and nitrogen and optionally substituted by hydrogen, hydroxy, alkyl, alkoxy, amino, azido or halogen.

24. A compound according to claim 21 or 23, where G and each Z are hydrogen.

25. A compound according to claim 22, where E, G and each Z are hydrogen.

26. A compound according to any one of claims 21–23, where at least one of F is arylamino and D is aryl.

27. A compound according to any one of claims 21–23, where F is arylamino and D is aryl.

28. A compound of claim 1, where A and B are independently $HOCH_2$ or $CH_3$, provided both A and B are not $CH_3$.

29. A compound of claim 2, where A and B are independently $HOCH_2$ or $CH_3$ provided both A and B are not $CH_3$.

30. A compound of claim 3, where A and B are independently $HOCH_2$ or $CH_3$ provided both A and B are not $CH_3$.

31. A compound of claim 28, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

32. A compound of claim 29, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

33. A compound of claim 30, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

34. A compound of claim 21, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

35. A compound of claim 22, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

36. A compound of claim 23, where F is phenylamino optionally substituted at any position by halogen, hydroxy, alkoxy, perhalo lower alkyl, carboxamido, amino, cyano or lower alkyl, and D is phenyl optionally substituted at any position by halogen, hydroxy, alkoxy, perhalo lower alkyl, carboxamido, amino, cyano or lower alkyl.

37. A compound according to any one of claims 28–36 where G and each Z are hydrogen.

38. A compound according to any one of claims 28, 29, 31, 32, 34, and 35 where E, G, and each Z are hydrogen.

39. A compound of claim 35, where D is phenyl and F is phenylamino substituted at any position by halogen or alkoxy.

40. A compound of claim 36, where D is phenyl and F is phenylamino substituted at any position by halogen or alkoxy.

41. A compound of any one of claims 1–3 where D is halogen or aryl.

42. A compound of any one of claims 1–3 where D is aryl.

43. A compound of any one of claims 1–3 where F is amino or arylamino.

44. A compound of any one of claims 1–3 where F is arylamino.

* * * * *

UNITED STATES PATENT AND TRADEMARK OFFICE
CERTIFICATE OF CORRECTION

PATENT NO. : 5,674,998
DATED : October 7, 1997
INVENTOR(S) : Serge H. BOYER et al.

It is certified that error appears in the above-indentified patent and that said Letters Patent is hereby corrected as shown below:

Foremost page, [63], Related U.S. Application Data, change "408,707, Sep. 18" to --408,107, Sep. 15--.

Column 1, line 11, change "408,707, filed Sep. 18" to --408,107, filed Sep. 15--.

Signed and Sealed this

Seventh Day of April, 1998

*Attest:*

BRUCE LEHMAN

*Attesting Officer*  Commissioner of Patents and Trademarks